US007994143B2

(12) United States Patent
Hostetler et al.

(10) Patent No.: US 7,994,143 B2
(45) Date of Patent: Aug. 9, 2011

(54) METABOLICALLY STABLE ALKOXYALKYL ESTERS OF ANTIVIRAL OR ANTIPROLIFERATIVE PHOSPHONATES, NUCLEOSIDE PHOSPHONATES AND NUCLEOSIDE PHOSPHATES

(75) Inventors: Karl Y. Hostetler, Del Mar (CA); James R. Beadle, San Diego, CA (US); Jacqueline Ruiz, San Diego, CA (US); Merrick R. Almond, Apex, NC (US); George R. Painter, Chapel Hill, NC (US); Timothy A. Riley, Huntsville, AL (US); Paula Francom, Salem, UT (US)

(73) Assignees: Chimerix, Inc., Durham, NC (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 12/797,327

(22) Filed: Jun. 9, 2010

(65) Prior Publication Data
US 2010/0249056 A1 Sep. 30, 2010

Related U.S. Application Data

(62) Division of application No. 11/736,614, filed on Apr. 18, 2007, now Pat. No. 7,749,983.

(60) Provisional application No. 60/746,318, filed on May 3, 2006.

(51) Int. Cl.
A01N 43/04 (2006.01)
A61K 31/70 (2006.01)

(52) U.S. Cl. ............... 514/43; 514/45; 514/46; 514/47; 514/48; 514/49; 514/50; 514/51; 514/52

(58) Field of Classification Search ............... None
See application file for complete search history.

(56) References Cited

U.S. PATENT DOCUMENTS

| 4,684,631 | A | 8/1987 | Hori et al. |
|---|---|---|---|
| 4,797,479 | A | 1/1989 | Shuto et al. |
| 5,512,671 | A | 4/1996 | Piantodosi et al. |
| 5,614,548 | A | 3/1997 | Piantadosi et al. |
| 5,633,235 | A | 5/1997 | Townsend et al. |
| 5,770,584 | A | 6/1998 | Kucera et al. |
| 5,827,833 | A | 10/1998 | Townsend et al. |
| 5,962,437 | A | 10/1999 | Kucera et al. |
| 6,030,960 | A | 2/2000 | Morris-Natschke et al. |
| 6,413,944 | B1 | 7/2002 | Townsend et al. |
| 6,670,341 | B1 | 12/2003 | Kucera et al. |
| 7,026,469 | B2 | 4/2006 | Kucera et al. |
| 7,129,227 | B1 | 10/2006 | Kucera et al. |
| 7,135,584 | B2 | 11/2006 | Kucera et al. |
| 7,141,557 | B2 | 11/2006 | Kucera et al. |
| 7,294,619 | B2 | 11/2007 | Kucera et al. |
| 7,294,620 | B2 | 11/2007 | Kucera et al. |
| 7,294,621 | B2 | 11/2007 | Kucera et al. |
| 2002/0082242 | A1 | 6/2002 | Kucera et al. |
| 2004/0161398 | A1 | 8/2004 | Kucera et al. |
| 2004/0259845 | A1 | 12/2004 | Kucera et al. |
| 2005/0080050 | A1 | 4/2005 | Kucera et al. |
| 2005/0187191 | A1 | 8/2005 | Kucera et al. |
| 2005/0187192 | A1 | 8/2005 | Kucera et al. |
| 2006/0264397 | A1 | 11/2006 | Kucera et al. |
| 2007/0099870 | A1 | 5/2007 | Kucera et al. |
| 2007/0105811 | A1 | 5/2007 | Kucera et al. |
| 2007/0105812 | A1 | 5/2007 | Kucera et al. |

FOREIGN PATENT DOCUMENTS

| EP | 0533825 B1 | 4/1996 |
|---|---|---|
| EP | 781138 A2 | 7/1997 |
| EP | 1228080 A2 | 8/2002 |
| EP | 0702556 B1 | 10/2002 |
| EP | 01389970 A1 | 2/2004 |
| EP | 01852121 A2 | 11/2007 |
| GB | 02166740 A | 5/1986 |
| JP | 61091195 | 5/1986 |
| JP | 61091196 | 5/1986 |
| JP | 61152694 | 7/1986 |
| JP | 61171498 | 8/1986 |
| JP | 61238797 | 10/1986 |
| JP | 62169797 | 7/1987 |
| JP | 62298597 | 12/1987 |
| JP | 05201870 | 8/1993 |
| JP | 07056033 | 3/2007 |
| WO | WO 89/07762 A1 | 8/1989 |
| WO | WO 90/04918 A2 | 5/1990 |
| WO | WO 91/19726 A1 | 12/1991 |
| WO | WO 96/06620 A3 | 8/1994 |
| WO | WO 94/28908 A3 | 12/1994 |
| WO | WO 01/34614 A3 | 5/2001 |
| WO | WO 02/087465 A2 | 11/2002 |
| WO | WO 2005/087788 | 9/2005 |
| WO | WO 2005/099719 A2 | 10/2005 |

OTHER PUBLICATIONS

Hostetler et al., Synthesis and antiretroviral activity of phospholipid analogs of azidothymidine and other antiviral nucleosides. *J. Biol. Chem.*, 265(11):6112-6117, Apr. 1990.
Hostetler et al., Enhanced inhibition of HIV replication by dideoxythymidine diphosphate diglyceride in HT4-6C cells in vitro. *Clin. Res.*, 38(1): 115A, 1990. (Abstract).
Hostetler et al., Phospholipid derivatives of dideoxythymidine (ddT) exhibit greatly increased potency against replication of HIV in CD4-HeLa cells. *J. Cell Biochem.*, Suppl. 14D, p. 152, 1990, (Abstract, L 423).
Kumar et al., Effect of stereoisomers of lipid analogs of zidovudine (AZT) on HIV-infected HT4-6C cells. *FASEB J.*, 4:(7), A2259, 1990. (Abstract, 3270).
Hostetler et al., Phosphatidylazidothymidine. Mechanism of antiretroviral action in CEM cells. *J. Biol. Chem.*, 266(18):11714-11717, Jun. 1991.

(Continued)

Primary Examiner — Patrick Lewis
(74) Attorney, Agent, or Firm — Swanson & Bratschun, L.L.C.

(57) ABSTRACT

The present invention relates to phosphonate, nucleoside phosphonate or nucleoside phosphate compounds, compositions containing them, processes for obtaining them, and their use in treating a variety of medical disorders, in particular viral infections, cancers and the like.

13 Claims, 3 Drawing Sheets

OTHER PUBLICATIONS van Wijk et al., Lipid conjugates of antiretroviral agents: release of antiretroviral nucleoside monophosphate by a nucleoside diphosphate diglyceride hydrolase activity from rat liver mitochondria. *Biochim. Biophys. Acta*, 1084:307-310, 1991.

van Wijk et al., Cytidine diphosphate diglyceride analogs of antiretroviral dideoxynucleosides: evidence for release of dideoxynucleoside-monophosphates by phospholipid biosynthetic enzymes in rat liver subcellular fractions. *Biochim. Biophys. Acta*, 1086:99-105, 1991.

van Wijk et al., Lipid conjugates of antiretroviral agents: release of antiretroviral nucleoside monophosphates by a nucleoside diphosphate diglyceride hydrolase activity from rat liver mitochondria. *Biochim Biophys Acta*, 1084:307-310, 1991.

van Wijk et al., Antiviral nucleoside diphosphate diglycerides: Improved synthesis and facilitated purification. *J. Lipid Res.*, 33:1211-1217, 1992.

Kumar et al., Equal inhibition of HIV replication by stereoisomers of phosphatidyl-AZT: Lack of stereospecificity of lysosomal phospholipase $A_1$. *J. Biol. Chem.*, 267(28):20288-20292, Oct. 1992.

Hostetler et al., Greatly enhanced inhibition of HIV-1 replication in CEM and HT4-6C cells by 3'-deoxythymidine diphosphate dimyristoylglycerol, a lipid prodrug of 3'-deoxythymidine. *Antimicrob. Agents Chemotherapy*, 36(9):2025-2029, Sep. 1992.

Hostetler et al., Acyclovir diphosphate dimyristoylglycerol: A phospholipid prodrug with activity against acyclovir-resistant herpes simplex virus, *Proc. Nat. Acad. Sci. USA*, 90:11835-11839, Dec. 1993.

van Wijk et al., Synthesis, characterization and some properties of cytidine diphosphate diglyceride analogs with antiretroviral activity. *Biochim. Biophys. Acta*, 1165:45-52, 1992.

Xie et al., Synthesis and antiviral activity of dipalmitoylphosphatidyldideoxyguanosine in hepatitis B virus infected cells, in vitro, *FASEB J.*, 7:1448, 1993. (Abstract).

van Wijk et al., Synthesis and antiviral activity of 3'-azido-3'-deoxythymidine triphosphate distearoyl glycerol. A novel phospholipid conjugate of the anti-HIV agent AZT. *Chemistry and Physics of Lipids*, 70:213-222, 1994.

Hostetler et al., Antiviral Activity of phosphatidyl-dideoxycytidine in hepatitis-B infected cells and enhanced hepatic uptake in mice, Antiviral Res., 24:59-67, 1994.

Hostetler et al., Phosphatidyl-dideoxycytidine and phosphatidyl-ddc: Assessment of uptake in mouse lymphoid tissues, antiviral activity in HIV-infected cells and in Rauscher leukemia virus infected mice, Antimicrobial Agents Chemotherapy., 38(12):2792-2797, Dec. 1994.

Shakiba et al., Antiviral effect in human cytomegalovirus-infected cells, pharmacokinetics and intravitreal toxicology in rabbits of acyclovir diphosphate dimyristoylglycerol, Antimicrobial Agents Chemotherapy., 39(6):1383-1385, Jun. 1995.

Xie et al., Phosphatidyl-2',3'-dideoxy-3'-thiacytidine: synthesis and antiviral activity in hepatitis B and HIV-1 infected cells, Antiviral Res., 28:113-120, 1995.

Korba et al., Liver-Targeted Antiviral Nucleosides: enhanced antiviral activity phosphatidyl-dideoxyguanosine Versus dideoxyguanosine in woodchuck hepatitis virus infection in vivo, Hepatology, 23(5):958-963, 1996.

Taskintuna et al., Evaluation of a novel lipid prodrug for intraocular drug delivery: effect of acyclovir diphosphate dimyristoylglycerol in a rabbit model with herpes simplex virus-1 retinitis, Retina, 17(1):57-64, 1997.

Hostetler et al., Antiviral activity of alkylglycerol foscarnet analogs in HIV-1 infected HT4-6C cells: structure-activity studies, 9th International Conf. on Antiviral Research, Fukushima, Japan, Antiviral Research, 30:A11, 1996. (Abstract).

Kini et al., Alkoxy Propane Prodrugs of Foscarnet: Effect of Alkyl Chain Length on In Vitro Antiviral Activity in Cells Infected with HIV-1, HSV-1 and HCMV, Antiviral Research, 36:43-53, 1997.

Rosowsky et al., Synthesis and in vitro antiviral activity of long chain 5'-(o-alkoxycarbonylphosphinytl)-3'-azido-3'-deoxythymidines against wild type and AZT- and foscarnet-resistant strains of human immunodeficiency type-1 virus (HIV-1), Proc. 10th Internat. Conf. Antiviral Research, Atlanta, Apr. 1997; Antiviral Res., 34(2): 10, 1997. (Abstract).

Beadle et al., Alkylthioglycerol prodrugs of foscarnet: oral bioavailability and structure-activity studies in human cytomegalovirus,herpes simplex virus type-1 and human immunodeficiency virus type-1 infected cells, Antiviral Chem. Chemotherapy., 9:33-40, 1998.

Cheng et al., Intravitreal toxicology of the 1-O-Octadecyl-sn-glycerol-3-phosphonoformate (ODG-PFA) and its carboxymethyl ester in liposome formulation. Investigative Ophthalmology and Visual Sciences, 39(4):S276, 1998. (Abstract, 1261-B142).

Cheng et al., Intravitreal toxicology in rabbits of two preparations of 1-O-octadecyl-sn-glycerol-3-phosphonoformate (ODG-PFA) a sustained delivery anti-CMV drug. Investigative Ophthalmology and Visual Sciences, 40(7):1487-1495, Jun. 1999.

Cheng et al., Intravitreal pharmacokinetics in rabbits of the foscarnet lipid prodrug: 1-O-octadecyl-sn-glycerol-3-phosphonoformate (ODG-PFA). Current Eye Research,18(3):161-167, 1999.

Cheng et al., Intravitreal toxicology and therapeutic efficacy of the carboxymethyl ester of the 1-O-octadecyl-sn-glycerol-3-phosphonoformate (ODG-PFA-OMe), a novel lipid anti-viral prodrug for intraocular drug delivery. Journal of Ocular Pharmacology and Therapeutics, 15(4):363-377, 1999.

Cheng et al., Treatment of herpes retinitis in an animal model with sustained delivery antiviral drug, liposomal 1-O-octadecyl-sn-glycero-3-phosphonoformate, Retina,19(4):325-331, 1999.

Beadle et al., Synthesis and antiviral evaluation of 1-O-hexadecylpropanediol-3-P-acyclovir: Efficacy against HSV-1 infection in mice, Nucleosides, Nucleotides & Nucleic Acids, 19(1&2):471-790, 2000.

Cheng et al., Intravitreal toxicology and treatment efficacy of a long acting antiviral lipid prodrug of ganciclovir in liposome formulation, Investigative Ophthalmology & Visual Science, 41(6):1523-1532, May 2000.

Hostetler et al., In Vitro and in Vivo Activity of 1-O-hexadecylpropanediol-3-phospho-ganciclovir and 1-O-hexadecylpropanediol-3-phospho-penciclovir in Cytomegalovirus and Herpes Simplex Virus Infections, Antiviral Chemistry and Chemotherapy, 12:61-70, 2001.

Hammond et al., Alkylglycerol prodrugs of phosphonoformate are potent in vitro inhibitors of nucleoside resistant HIV type 1 and select for resistance mutations that suppress zidovudine resistance, Antimicrobial Agents Chemotherapy, 45(6):1621-1628, Jun. 2001.

Kern et al., Enhanced inhibition of orthopoxvirus replication in vitro by alkoxyalkyl esters of cidofovir and cyclic cidofovir, Antimicrobial Agents Chemotherapy, 46(4):991-995, Apr. 2002.

Huggins et al., Orally active ether lipid prodrugs of cidofovir for the treatment of smallpox, Antiviral Research, 53:A66(104), 2002. (Abstract).

Beadle et al., Alkoxyalkyl esters of cidofovir and cyclic cidofovir exhibit multiple log enhancement of antiviral activity against cytomegalovirus and herpesvirus replication, in vitro, Antimicrobial Agents Chemotherapy, 46(8):2381-2386, Aug. 2002.

Aldern et al., Increased antiviral activity of 1-O-hexadecyloxypropyl-cidofovir in MRC-5 human lung fibroblasts is explained by unique cellular uptake and metabolism, Molecular Pharmacology, 63(3):678-681, 2003.

Ciesla et al., Esterification of cidofovir with alkoxyalkanols increases oral bioavailability and diminishes drug accumulation in kidney, Antiviral Research 59:163-171, 2003.

Smee et al., Effects of four antiviral substances on lethal vaccinia virus (IDH strain) respiratory infections in mice, International J. Antimicrobial Agents, 23(5):430-437, 2004.

Quenelle et al., Oral treatment of cowpox and vaccinia infections in mice with ether lipid esters of cidofovir, Antimicrobial Agents Chemotherapy, 48(2):404-412, Feb. 2004.

Keith et al., Inhibitory activity of alkoxyalkyl and alkyl esters of cidofovir and cyclic cidofovir against orthopoxvirus replication, in vitro, Antimicrobial Agents Chemotherapy, 48(5):1869-1871, May 2004.

Aldern et al., Cellular Uptake of Cidofovir and Various Alkoxyalkyl Esters of Cidofovir in MRC-5 Cells: Comparison with Antiviral Activity. Antiviral Research, 62(2), 103, A69, 2004 (Abstract).
Beadle et al., Direct Synthesis of Acyclic Nucleoside Phosphonate Alkoxyalkyl Monoesters. Antiviral Research, 62(2), 98, A66, 2004 (Abstract).
Keith et al., In Vitro Activity of Alkyl Esters of Cidofovir and Cyclic Cidofovir Against Orthopoxvirus Replication: Comparison of Activity with Alkoxyalkyl Esters. Antiviral Research, 62(2), 107, A70, 2004 (Abstract).
Hartline et al., Activity of Ether Lipid Esters of Acyclic Nucleoside Phosphonates Against Adenovirus Replication In Vitro. Antiviral Research, 62(2), 116, A73, 2004 (Abstract).
Wan et al., Comparative Antiviral Activity of Alkyl and alkoxyalkyl Esters of Cidofovir Against HCMV Infected Cells, In Vitro. Antiviral Research, 62(2), 71, A55, 2004 (Abstract).
Evans et al., Inhibition of Orthopoxvirus DNA Polymerases by Cidofovir Diphosphate: In Vitro Enzymatic Studies Using Highly Purified Vaccinia Virus DNA Polymerase, Antiviral Research, 62(2), 74, A57, May 2004 (Abstract).
Ruiz et al., Synthesis and Antiviral Activity of 9-[(3-hexadecyl-oxypropyl-phosphono)-1-propyloxymethyl]guanine, Antiviral Research, 62(2), 97, A66, 2004 (Abstract).
Trahan et al., HDP-(S)HPMPA: Oral Pharmacokinetics and Antiviral Activity Against Orthopoxvirus and Murine CMV Infections in Mice, Antiviral Research, 62(2), 108, A71, 2004 (Abstract).
Valiaeva et al., Synthesis and Antiviral Activity of 5-Substituted Hexadecyloxypropyl-1-[2-(phosphonomethoxy)-ethyl] cytosine (PMEC) Derviatives, Antiviral Research, 62(2), 99, A67, 2004 (Abstract).
Quenelle et al., Oral treatment of cowpox and vaccinia virus infections in mice with ether lipid esters of cidofovir. Antimicrob Agents Chemother., 48(2):404-412, Feb. 2004.
Bidanset, D.J., et al., Oral activity of ether lipid prodrugs of cidofovir against experimental human cytomegalovirus infections, J Infect Dis., 190(3):499-503, Aug. 2004.
Kern et al., Oral treatment of murine cytomegalovirus infections with ether lipid esters of cidofovir, Antimicrobial Agents Chemotherapy, 48(9):3516-3522, Sep. 2004.
Buller et al., Efficacy of oral active ether lipid analogs of cidofovir in a lethal mousepox model. Virology, 318(2):474-481, 2004.
Smee et al., Effects of four antiviral substances on lethal vaccinia virus (IHD strain) respiratory infections in mice. Int J Antimicrob Agents, 23(5):430-437, 2004.
Keith et al., Inhibitory activity of alkoxyalkyl and alkyl esters of cidofovir and cyclic cidofovir against orthopoxvirus replication in vitro. Antimicrob Agents Chemother., 48(5):1869-1871, May 2004.
Painter et al., Design and development of oral drugs for the prophylaxis and treatment of smallpox infection, Trends in Biotechnology, 22(8):423-427, Aug. 2004.
Hartline et al., Ether Lipid-Ester Prodrugs of Acyclic Nucleoside Phosphonates Activity Against Adenovirus Replication in Vitro, J Infect Dis., 191(3):396-399, Feb. 2005.
Cheng et al., Characterization of a Novel Intraocular Drug-Delivery System Using Crystalline Lipid Antiviral Prodrugs of Ganciclovir and Cyclic Cidofovir, Invest Ophthalmol Vis Sci.; 45(11):4138-4144 Nov. 2004.
Wan et al., Comparison of the antiviral activity of alkoxyalkyl and alkyl esters of cidofovir against human and murine cytomegalovirus replication in vitro, Antimicrobial Agents Chemotherapy, 49(2):656-662, Feb. 2005.
Magee et al., Mechanism of inhibition of vaccinia virus DNA polymerase by cidofovir diphosphate, Antmicrobial Agents Chemotherapy, 49(8):3153-3162, Aug. 2005.
Lut al., Intraocular properties of Hexadecyloxypropyl-cyclic-Cidofovir in Guinea Pigs, J. Ocular Pharmacology & Therapeutics, 21(3):205-209, 2005.
Williams-Aziz et al., Comparative Activity of Lipid Esters of Cidofovir and Cyclic Cidofovir Against Replication of Herpesviruses in Vitro, Antimicrobial Agents & Chemotherapy, 49(9):3724-3733, Sep. 2005.
Aldern et al., Alkoxyalkyl esters of (S)-HPMPA are potent inhibitors of HIV-1 in vitro, Antiviral Research, 65(3):41, A47, 2005 (Abstract).
Buller et al., Efficacy of smallpox vaccination in the presence of antiviral drugs, cidofovir and hexadecyloxypropyl-cidofovir, Antiviral Research, 65(3):72, A80, 2005 (Abstract).
Quenelle et al., Effect of oral treatment with HDP-(S)-HPMPA or ODE-(S)-HPMPA on cowpox or vaccinia virus infections in mice, Antiviral Research, 65(3):76, A81, 2005.
Ruiz et al., Synthesis and antiviral activity of alkoxyalkylesters of cidofovir monophosphate, Antiviral Research, 65(3):130, A91, 2005 (Abstract).
Choo et al., Novel 5-phosphono-pent-2-en-l-yl nucleosides (PPen-Ns) and their alkoxyalkyl phosphonoesters: Synthesis and antiviral evaluation, Antiviral Research, 65(3):132, A91, 2005 (Abstract).
Trahan et al., Lung targeted antivirals: studies with 1-O-octadecyl-2-O-benzyl-sn-glycero-3-cidofovir, Antiviral Research. 65(3):134, A92, 2005 (Abstract).
Andrei et al. Activity of alkoxyalkyl and alkyl esters of (S)-3-hydroxy-2-phosphonylmethoxypropyl derivatives of cytosine (HPMPC) and adenine (HPMPA) and cyclic cidofovir against orthopoxviruses, Antiviral Research, 65(3):136, A92, 2005. (Abstract).
Smee et al., Characterization and treatment of cidofovir-resistant vaccinia (WR strain) virus infections in cell culture and in mice. Antiviral Chem Chemother., 16:203-211, 2005.
Hartline et al., Inhibition of Herpesvirus Replication by a Series of Alkoxyalkyl Esters of Purine and Pyrimidine Based Nucleoside Phosphonates, Antiviral Research, A69 (59), 2006. (Abstract).
Quenelle, et al., Effect of Oral Treatment with (S)-HPMPA, HDP-(S)-HPMPA or ODE-(S)-HPMPA on Replication of Human Cytomegalovirus (HCMV) or Murine Cytomegalovirus (MCMV) Infection in Animal Models, Antiviral Research, A70 (67), 2006. (Abstract).
Aldern, et al., Comparison of the Intracellular Metabolism of Cidofovir and (S)-HPMPA and Their Hexadecyloxypropyl Esters, Antiviral Research., A57 (126), 2006. (Abstract).
Valiaeva et al., Alkoxyalkyl esters of phosphonomethoxyethyl purines: Synthesis and antiviral activity against HIV-1, in vitro. Antiviral Research, A42 (46), 2006. (Abstract).
Ruiz, et al., Antiviral Activity and Metabolic Stability and Branched Methyl Alkoxyalkyl Esters of Cidofovir Against Vaccinia, Cowpox and Ectromelia Viruses, in vitro. Antiviral Research, A57 (128), 2006. (Abstract).
Hostetler et al., Phospholipid prodrugs of antiviral nucleosides and HIV protease inhibitors: synthesis and biological activity. J. Molecular Recognition, 5:24, 1992 (Abstract).
Hostetler et al., Lipid prodrugs of phosphonoacids: greatly enhanced antiviral activity of 1-O-octadecyl-sn-glycero-3-phosphonoformate in HIV-1, HSV-1 and HCMV-infected cells, in vitro, Antiviral Research, 31:59-67, 1996.
Hostetler et al., Enhanced oral absorption and antiviral activity of 1-O-octadecyl-sn-glycero-3-phospho-acyclovir and related compounds in hepatitis B virus infection, in vitro, Biochemical Pharmacology, 53:1815-1822, 1997.
Rosowsky et al., Synthesis and in vitro activity of long-chain 5'-O-[(alkoxycarbonyl)phosphinyl]-3'-azido-3'-deoxythymidines against wild type and AZT- and foscarnet-resistant strains of HIV-1, J. Med. Chem., 40:2482-2490, 1997.
Hostetler et al., In vitro anti-HIV-1 activity of sn-2 substituted 1-O-octadecyl-sn-glycero-3-phosphonoformate analogues and synergy with zidovudine, Antiviral Chemistry and Chemotherapy, 11:213-220, 2000.
Hostetler et al., Antiviral activities of oral 1-O-hexadecylpropanediol-3-phosphoacyclovir and acyclovir in woodchucks with chronic woodchuck hepatitis virus infection, Antimicrobial Agents Chemotherapy, 44(7):1964-1969, Jul. 2000.
Cheng et al., Treatment or Prevention of Herpes Simplex Virus Retinitis with Intravitreally Injectable Crystalline 1-O-Hexadecylpropanediol-3-Phospho-Ganciclovir, Investigative Ophthalmology & Visual Science, 43(2):515-521, Feb. 2002.
Buller et al., Effect of oral ether lipid analogs of cidofovir on mortality and viral infectivity levels in tissues in a lethal ectromelia virus challenge model, Antiviral Research, 62(2), 131, A79, 2003. (Abstract).

Valiaeva et al., Effects of 9-[2-(phosphonomethoxy)ethyl]guanine (PMEG), hexadecyloxypropyl-PMEG and octadecyloxyethyl-PMEG on replication of HIV-1, herpesviruses and poxviruses, in vitro, Antiviral Research, 62(2), 111, A72, 2003. (Abstract).

Aldern et al., Alkoxyalkyl esters of adefovir: antiviral activity against cytomegalovirus and HIV-1, in vitro, Antiviral Research, 62(2), 101, A69, 2003 (Abstract).

Trahan et al., Oral pharmacokinetics and tissue distribution of 1-O-hexadecyloxypropyl-[2-14C]cyclic cidofovir in mice, Antiviral Research, 62(2), 132, A79, 2003. (Abstract).

Ciesla et al., Synthesis of alkoxyalkyl esters of (R)- and (S)-HPMPA and antiviral activity against herpesviruses, in vitro, Antiviral Research, 62(2), 102, A70, 2003 (Abstract).

Keith et al., Inhibitory effect of alkoxyalkyl esters of acyclic nucleoside phosphonates against orthopoxvirus replication, Antiviral Research, 62(2), 110, A72, 2003. (Abstract).

Buller et al., Efficacy of oral active ether lipid analogs of cidofovir in a lethal mousepox model, Virology, 318(2):474-481, 2004.

Kumar et al., Antiretroviral effects of glycerophospholipid stereoisomers of AZT on HIV replication in HT4-6C cells. Proc. 6th Internat. Conf. AIDS, San Francisco, vol. 1, p. 186, 1990 (Abstract).

Stuhmiller et al., Synthesis and antiviral activity of phospholipid derivatives of 1-(2'-deoxy-2'-fluoro-β-D-arabinofuranosyl)-5-iodouracil (FIAU) and 1-(2'-deoxy-2'-fluoro-β-D-arabinofuranosyl)-5-iodocytidine (FIAC). Proc. 200th Annual Meeting Am. Chem. Soc. (Medicinal) 133, 1990 (Abstract).

Hostetler, et al., PhosphatidylddC, A phospholipid prodrug of dideoxycytidine: antiviral properties and improved pharmacokinetics in mice. Proc. 7th Internat. Conf. AIDS, Florence, Italy, W.A. 1001, 1991 (Abstract).

van Wijk et al., Phospholipid conjugates of dideoxynucleosides; the metabolism of dideoxycytidine- and 3'-deoxythymidine diphosphate diglyceride in rat liver. Proc. 7th Internat. Conf. AIDS, Florence, Italy, W.A.1092, 1991 (Abstract).

Xie et al., Synthesis, purification and antiviral evaluation of a phospholipid conjugate of (−)-2'-deoxy-3'-thiacytidine (3TC) in vitro, Proc. 207th Mtg. Am. Chem. Soc. (Medicinal), 32, 1994 (Abstract).

Hostetler et al., Phosphonoacid prodrugs with greatly increased antiviral activity in HCMV-infected cells, in vitro, Proc. 8th. Internat. Soc. Antiviral Res., Santa Fe, NM, 1995 (Abstract).

Hostetler et al., 1-O-Octadecylglycerol-3-phosphonoformate exhibits enhanced activity and synergy with AZT against HIV, in vitro, Proc. 35th Intersci. Conf. Antimicrobial Agents & Chemotherapy, San Francisco, 1995 (Abstract).

Kini et al., Synthesis and antiviral activity of stereoisomers of 1-O-octadecyl-sn-glycero-3-phosphonoformate, Proc. 210th American Chemical Society Meeting, 101, 1995 (Abstract).

Beadle et al., Synthesis and antiviral activity of alkoxypropyl esters of ganciclovir monophosphate in HCMV- and HSV-infected cells, Proc. 213th Am. Chemical Soc., 268, 1997 (Abstract).

Kini et al., Lipid prodrug of a foscarnet-AZT conjugate: synthesis and antiviral activity against PFA- and AZT-resistant strains of HIV, Proc. 213th Am Chemical Soc., 283, 1997.

Aldern et al., Antiviral activity of lipid prodrugs of foscarnet and ganciclovir against the AD169 and Toledo strains of human cytomegalovirus. Proc. 11th Internat. Conf. Antiviral Research, California, Apr. 1998 (Abstract).

Wright et al., The effect of intraperitoneal injection of 1-O-octadecyl-sn-glycero-3-foscarnet and its carboxymethyl ester on mortality and serum calcium levels in mice. Proc. 11th Internat. Conf. Antiviral Research, California, Apr. 1998 (Abstract).

Korba et al., Phospholipid prodrugs of antiviral nucleosides: efficacy of orally administered 3-hexadecyloxypropane-1-phospho-acyclovir against hepatitis B infection in woodchucks. Proc. 11th Internat. Conf. Antiviral Research, California, Apr. 1998 (Abstract).

Kini et al., Anti-hepatitis B virus activity of 3-hexadecyloxypropane-1-phospho-penciclovir and 3-hexadecyloxypropane-1-phospho-dideoxyguanosine in 2.2.15 cells. Proc. 11th Internat. Conf. Antiviral Research, California, Apr. 1998 (Abstract).

Hostetler et al., Alkylglycerol foscarnet analogs are active in vitro at submicromolar concentrations against a panel of drug resistant strains of HIV-1, Proc. 7th Conference on Retroviruses and Opportunistic Infections, Jan. 30, 2000 (Abstract).

Beadle et al., Alkylglyceryl and Alkoxyalkyl Esters of Antiviral Phosphonates, Proc. 14th Int. Conf. Antiviral Research, 2001 (Abstract).

Winegarden et al., Oral pharmacokinetics and preliminary toxicology of 1-O-hexadecyloxypropyl-cidofovir in mice, Antiviral Research, 53:A67(105), 2002 (Abstract).

Aldern,et al., 1-O-Hexadecyloxypropyl-[14C]cidofovir: cellular uptake and metabolism in MRC-5 human lung fibroblasts, in vitro, Antiviral Research, 53:A62 (92), 2002 (Abstract).

Wan et al., Alkoxyalkyl Esters of Cidofovir and cyclic cidofovir: effects of alkyl chain length, unsaturation and substitution on the in vitro antiviral activity in cells infected with HSV-1 and HCMV, Presentation at the American Chemical Society, Medicinal Chemistry Meeting, Boston, MA, Aug. 2002 (Abstract).

Wu et al., A novel intravitreally injectable, crystalline prodrug of 5-fluorouracil (HDP-5F2'du) for sustained intraocular drug delivery to treat pathologic intraocular proliferation, National meeting of ARVO, #471, Miami, 2005 (Abstract).

Hostetler, et al., Oral activity of 1-O-hexadecylpropanediol-3-P-acyclovir in woodchucks with chronic woodchuck hepatitis virus infection and synergy with lamivudine in vitro. Abstracts of the 3rd Int. Conf. On Therapies for Viral Hepatitis, Antiviral Therapy, 4(4), 27, A80, Dec. 1999.

Wan et al., Alkoxyalkyl esters of cidofovir with improved antiviral potency and selectivity: In search of the optimal ester. Abstracts of the Interscience Conference on Antimicrobial Agents and Chemotherapy, 42, p. 430 Sep. 2002.

Hostetler et al. (Oct. 1989) Academy Workshop on Intracellular and Intravascular Lipid Transport.

Beadle et al. (2006) J. Med. Chem. 49:2010-2015, "Synthesis and Antiviral Evaluation of Alkoxyalkyl Derivatives of 9-(S)-(3-Hydroxy-2-phosphonomethoxypropryl)adenine against Cytomegalovirus and orthopoxviruses".

Hong et al. (1995) Journal of Lipid Mediators and Cell Signaling 10(1-2):159-161, "Nucleoside-ether lipid conjugates as biotransformed prodrugs of antitumour and antiviral nucleosides".

Masuda et al. (2003) Boorganic and Medicinal Chemistry Letters 13:669-673, "Synthesis and Anti-Influenza Evaluation of Orally Active Bicyclic Ether Derivatives Related to Zanamivir".

Kern et al. (2002) Antimicrobial Agents and Chemotherapy 46:991-995, "Oral Treatment of Murine Cytomegalovirus Infections with Ether Lipid Esters of Cidofovir".

International Search Report issued Aug. 21, 2008 in PCT/US2007/066822 (attached).

hexadecyloxypropyl cidofovir (HDP-CDV) - *not metabolically stable*

Examples of Metabolically Stable Esters of Cidofovir

Note that the same strategy can be applied to other nucleoside phosphonates such as HPMPA, cyclic HPMPA, cyclic CDV, tenofovir, PMEG, PPen-G as well as to nucleoside phosphate alkoxyalkyl esters

METABOLICALLY STABLE ALKOXYALKYL ESTERS OF ANTIVIRAL OR ANTIPROLIFERATIVE PHOSPHONATES, NUCLEOSIDE PHOSPHONATES AND NUCLEOSIDE PHOSPHATES

RELATED APPLICATIONS

This application is a divisional application of U.S. application Ser. No. 11/736,614, filed Apr. 18, 2007, now U.S. Pat. No. 7,749,983 which claims priority to U.S. Application Ser. No. 60/746,318, filed May 3, 2006, each of which is entitled "Metabolically Stable Alkoxyalkyl Esters of Antiviral or Antiproliferative Phosphonates, Nucleoside Phosphonates and Nucleoside Phosphates." Each of these applications is incorporated herein by reference in its entirety.

FIELD OF THE INVENTION

The present invention relates to orally administered drugs for treatment of viral infections and certain cancers. In particular, the present invention relates to metabolically stable alkoxyalkyl esters of phosphonates, nucleoside phosphonates and nucleoside phosphates, compositions containing them, processes for obtaining them, and their use in treating a variety of medical disorders, in particular viral infections, cancers and the like.

BACKGROUND OF THE INVENTION

Nucleoside phosphonates have antiviral, antiproliferative and a variety of other therapeutic benefits. Among these are the antiviral nucleoside phosphonates, such as, for example, cidofovir, cyclic cidofovir, adefovir, tenofovir, and the like, as well as the 5'-phosphonates and methylene phosphonates of azidothymidine (AZT), ganciclovir, acyclovir, and the like. In these compounds, the 5'-hydroxyl of the sugar moiety, or its equivalent in acyclic nucleosides (ganciclovir, penciclovir, acyclovir) which do not contain a complete sugar moiety, is replaced with a phosphorus-carbon bond. In the case of the methylene phosphonates, a methylene group replaces the 5'-hydroxyl or its equivalent, and its carbon atom is, in turn, covalently linked to the phosphonate.

Upon cellular metabolism of nucleoside phosphonates, two additional phosphorylations occur to form the nucleoside phosphonate diphosphate which represents the equivalent of nucleoside triphosphates. Antiviral nucleoside phosphonate diphosphates are selective inhibitors of viral RNA or DNA polymerases or reverse transcriptases. That is to say, their inhibitory action on viral polymerases is much greater than their degree of inhibition of mammalian cell DNA polymerases α, β and γ or mammalian RNA polymerases. Conversely, the antiproliferative nucleoside phosphonate diphosphates inhibit cancer cell DNA and RNA polymerases and may show much lower selectivity versus normal cellular DNA and RNA polymerases.

As noted above, one class of antiviral and antiproliferative compounds are the antiviral nucleoside phosphonates. Two representative structures of this class of compounds, namely CDV and HPMPA, are set forth below:

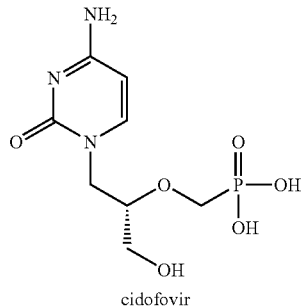
cidofovir

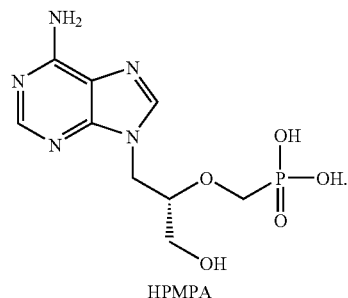
HPMPA

Another class of phosphonates is the 5'-phosphonates and methylene phosphonates of azidothymidine, ganciclovir, acyclovir, and the like. In compounds of this type, the 5'-hydroxyl of the sugar moiety, or its equivalent in acyclic nucleosides (ganciclovir, penciclovir, acyclovir), which do not contain a complete sugar moiety, is replaced with a phosphorus-carbon bond. In the case of the methylene phosphonates, a methylene group replaces the 5'-hydroxyl or its equivalent, and its carbon atom is, in turn, covalently linked to the phosphonate. Two representative structures of this class of compounds, namely AZT 5'-phosphate and AZT 5'-phosphonate, are set forth below.

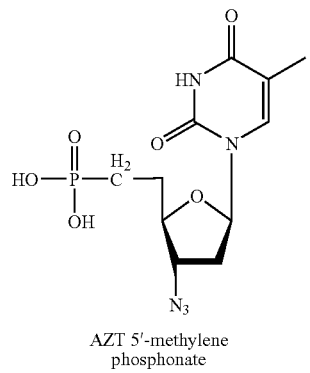
AZT 5'-methylene phosphonate

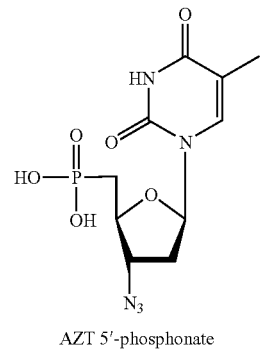
AZT 5'-phosphonate

Another class of therapeutically effective compounds is the nucleoside phosphates, such as, acyclovir monophosphate, 2'-O-methyl-guanosine-5'-phosphate, 2'-O-methyl-cytidine-5'-phosphate and 2'-C-methyl-cytidine-5'-phosphate. Two representative structures of this class of compounds are set forth below:

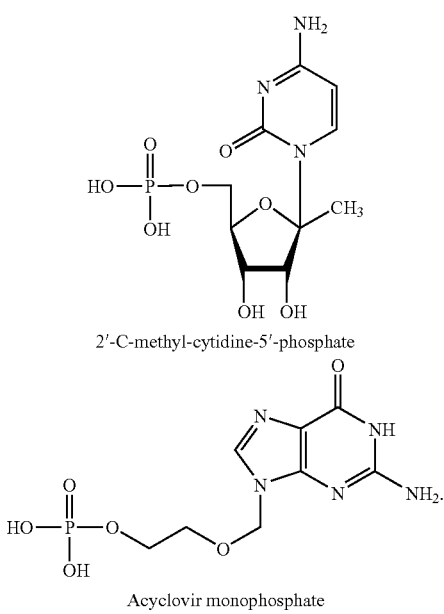

2'-C-methyl-cytidine-5'-phosphate

Acyclovir monophosphate

Yet another class is the antiviral phosphonates, phosphonoformate and phosphonoacetate as illustrated below.

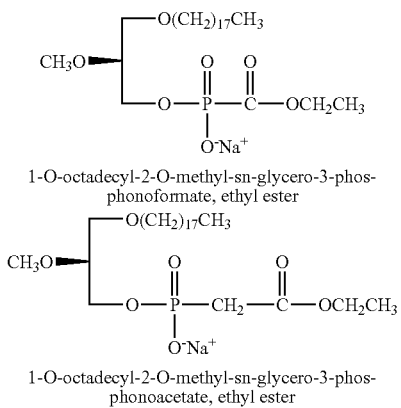

1-O-octadecyl-2-O-methyl-sn-glycero-3-phosphonoformate, ethyl ester

1-O-octadecyl-2-O-methyl-sn-glycero-3-phosphonoacetate, ethyl ester

Various substituent groups may be attached to phosphonates and phosphates to produce derivatives having various degrees of pharmacological potency. One class of derivative compounds are the alkoxyalkyl esters, such as hexadecyloxypropyl cidofovir (HDP-CDV), which is illustrated by the following general structure:

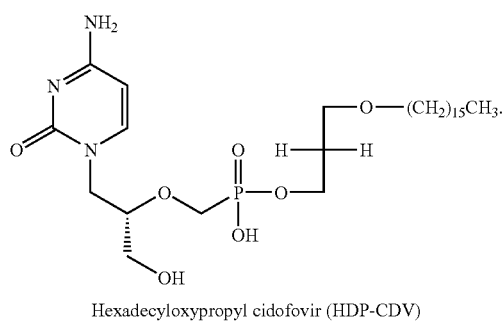

Hexadecyloxypropyl cidofovir (HDP-CDV)

CDV itself is not orally active; however esterification of CDV with certain alkoxyalkanols such as hexadecyloxypropanol dramatically increases its antiviral activity and selectivity in vitro and confers a degree of oral bioavailability. The alkyl chain length of these CDV analogs is related to solubility and the ability of the compounds to associate with biomembranes.

Although alkoxyalkyl esters of nucleoside phosphates and phosphonates, such as hexadecyloxypropyl-cidofovir (HDP-CDV), have therapeutically beneficial properties, they suffer from pharmacological disadvantages as orally administered agents. Orally administered drugs are usually taken up from the small intestine into the portal vein, which exposes the drug to potentially rapid lipid metabolism in the enterocytes of the small intestines and in the liver. Alkoxyalkyl esters of phosphates and phosphonates, such as HDP-CDV can be incorporated into cell membranes where the phosphate or phosphonate is subsequently liberated inside the cell or can be oxidatively metabolized by the cytochrome P450s such as CYP3A4 in the liver or intestine leading to omega oxidation of the alkyl chain followed by beta oxidation. It has recently been determined that alkoxyalkyl esters of phosphates and phosphonates can be oxidized at the terminal end of the alkyl chain by omega oxidation and are further degraded by beta oxidation to short chain inactive metabolites. This process, which is illustrated in FIG. 1 for nucleoside monophosphonate HDP-CDV, may be very rapid and is deleterious to the intended pharmacologic effect of the compounds. In the case of HDP-CDV, the inactive metabolite is water soluble, virologically inactive, and rapidly excreted in the urine. Rapid metabolism by this pathway may lower plasma levels of the prodrug, and reduce the antiviral efficacy of HDP-CDV and alkoxyalkyl esters of phosphonates, nucleoside phosphonates and nucleoside phosphates.

There is therefore a continuing need for more stable pharmaceutical agents to treat a variety of disorders, such as those caused by viral infection and inappropriate cell proliferation, e.g. cancer. Thus, it is an object of the present invention to develop chemically modified phosphonates, nucleoside phosphonates and nucleoside phosphates that can slow the metabolism of oral antiviral and anticancer compounds.

SUMMARY OF THE INVENTION

The present invention includes esters of phosphonates, nucleoside phosphonates and nucleoside phosphates (referred to collectively hereinafter as esters) that are resistant to metabolic inactivation resulting from oxidation of these compounds in the liver. More specifically, the present invention includes terminal or penultimate branched chain, unsaturated and halogen substituted alkoxyalkyl esters of phosphonate compounds, wherein said substituents stabilize these compounds by providing metabolic stability during absorption in the small intestine, first pass liver metabolism and subsequent distribution to peripheral tissues. Included in the present invention are methods for using said esters for treating various diseases and conditions.

The compounds and methods of this invention are based upon the unique insight that ω-oxidation of lipid esters of phosphonates and phosphates may be slowed by placing a blocking group or groups at or near the penultimate carbon of the alkyl chain. Potential blocking groups include, but are not limited to alkyl groups, including, but not limited to methyl, ethyl and propyl, cyclopropyl and halogens. Potential blocking groups also include alkenyl groups containing one or more double bonds, including a terminal double bond. Although substituted alkoxyalkyl phosphates and alkylglycerol phosphates are known in the art, the use of penultimate or terminally substituted alkyl chains to stabilize lipid phosphate or phosphonate ester drugs against rapid omega and beta oxidation has not been reported previously. Phosphonate compounds contemplated for use in accordance with the present invention include those having antiviral and antiproliferative activity.

Representative examples of the phosphonate compounds and esters thereof contemplated for use in accordance with the present invention are set forth in the references cited in Table 1. Also included within the scope of the instant invention are nucleoside analogs with antiviral activity against hepatitis C, which can be converted to their alkoxyalkyl 5'-phosphates or their alkylglycerol phosphates. Examples of nucleosides in this class of compounds include, but are not limited to 2'-C-methyl adenosine, 2'-C-methyl guanosine, 7-deaza-2'-methyl adenosine, 2'-C-methyl cytosine. Other nucleosides and analogs thereof contemplated for use in accordance with this invention following conversion to their alkoxyalkyl 5'-phosphates or their alkylglycerol phosphates are set forth in the references cited in Table 2.

Further included are nucleoside analogs with antiviral activity against hepatitis B, which may be converted to their 5'-phosphates, 5'-phosphonates or 5'-methylene phosphonates. Exemplary nucleosides in this class of compounds include, but are not limited to 3TC, FTC, DAPD, L-FMAU, entecavir, telbivudine and various β-L-2'-deoxycytidine, β-L-2'-deoxyadenine and β-L-2'-deoxythymidine analogs described by Bryant et al. ((January 2001) Antimicrob Agents Chemother 45(1):229-235).

Anticancer agents may also be derivatized according to the method of this invention. Some subject compounds include but are not limited to (E)-2'-deoxy-2'-fluoromethylene-cytidine (FMdC) and 1-(2-deoxy-2-fluoro-4-thio-β-D-arabinosyl)cytosine (4'-thio-FAC). Other antiproliferative nucleosides may also become active when derivatized according to the invention including, but not limited to Ara-C, Ara-G, 5-fluorouridine, 5-fluoro-deoxyuridine, fludarabine, gemcitabine, decitabine or alkylglycerol phosphate or alkoxyalkyl phosphate esters of taxol. Non-nucleoside cancer agents may be similarly derivatized with the metabolically stable alkoxyalkyl groups of the invention including, but not limited to topotecan by phosphorylating and esterifying an available hydroxyl group. Etoposide may be derivatized by attaching metabolically stable groups of the invention to the phosphate residue of etoposide.

Phosphonate and phosphate analogs contemplated for use in accordance with the present invention are selected to improve the bioactivity, selectivity, and/or bioavailability of the antiviral or antiproliferative compounds.

In another aspect of the present invention, there are provided pharmaceutical formulations containing the analogs of the phosphonate compounds described herein.

In yet another aspect of the present invention, there are provided a variety of therapeutic methods, e.g. methods for treating viral infections and methods for treating disorders caused by inappropriate cell proliferation, e.g. cancer and the like.

DETAILED DESCRIPTION OF THE PREFERRED EMBODIMENT

Figure 1:
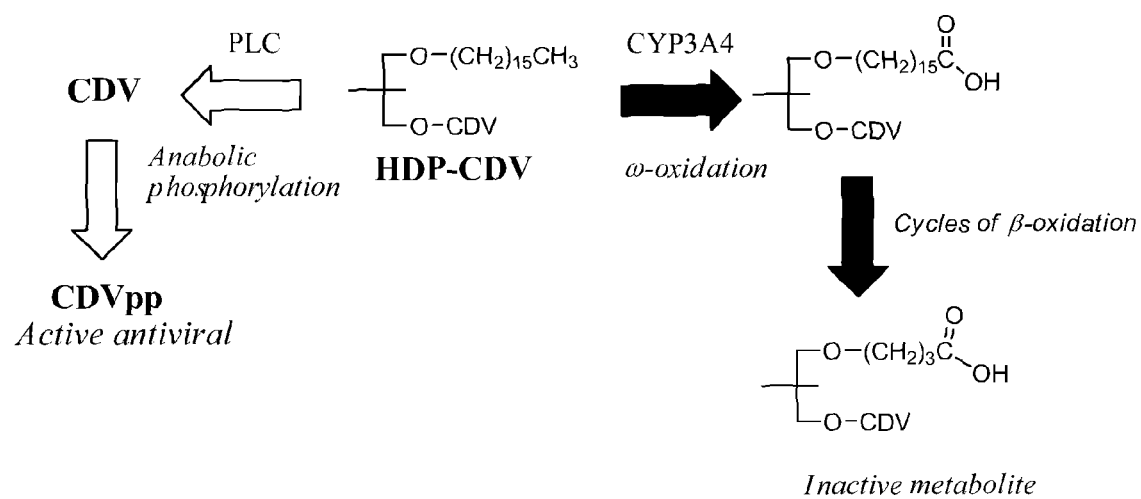
FIG. 1 illustrates schematically antiviral activation and metabolic inactivation pathways for hexadecyloxypropyl cidofovir (HDP-CDV).

The present invention includes chemical methods for synthesizing alkoxyalkyl esters having certain moieties at or near the omega end of the alkyl chain which block or slow degradation and metabolic inactivation. Specifically, the present invention includes terminal or penultimate branched chain, unsaturated and halogen substituted esters of phosphonate compounds, wherein said substituents stabilize these compounds by providing resistance to oxidation. Phosphonates, nucleoside phosphonates and nucleoside phosphates having antiviral or anticancer activity are subjects of the invention.

Various terms are used herein to refer to aspects of the present invention. To aid in the clarification of the description of the components of this invention, the following definitions are provided.

It is to be noted that the term "a" or "an" entity refers to one or more of that entity; for example, a phosphonate refers to one or more phosphonates. As such, the terms "a" or "an", "one or more" and "at least one" are used interchangeably herein.

It is also to be noted that in some cases for purposes of illustration only a single stereoisomer is depicted for a particular compound. However, the method of the invention is not limited to any particular isomer and can be extended to the S enantiomer, the R enantiomer or racemic mixtures thereof.

As used herein, the term "prodrug" refers to derivatives of pharmaceutically active compounds that have chemically or metabolically cleavable groups and become the pharmaceutically active compound by solvolysis or under in vivo physiological conditions.

The term "purine or pyrimidine base" includes, but is not limited to, 6-alkylpurine and $N^6$-alkylpurines, $N^6$-acylpurines, $N^6$-benzylpurine, 6-halopurine, $N^6$-acetylenic purine, $N^6$-acyl purine, $N^6$-hydroxyalkyl purine, 6-thioalkyl purine, $N^2$-alkylpurines, 7-deazapurines, $N^4$-alkylpyrimidines, $N^4$-acylpyrimidines, 4-halopyrimidines, $N^4$-acetylenic pyrimidines, 4-amino and $N^4$-acyl pyrimidines, 4-hydroxyalkyl pyrimidines, 4-thioalkyl pyrimidines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Included in this definition are ring-expanded and open-ring cogeners of any of the aforementioned purines. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl. Preferred bases include cytosine, 5-fluorocytosine, uracil, thymine, adenine, guanine, xanthine, 2,6-diaminopurine, 6-aminopurine, 6-chloropurine and 2,6-dichloropurine.

The term "alkyl" as used herein, unless otherwise specified, refers to a saturated straight or branched hydrocarbon.

The alkyl group can be optionally substituted with one or more halogens selected from the group consisting of F, Cl, Br or I.

The term "alkenyl" as used herein, unless otherwise specified, refers to a partially unsaturated straight or branched hydrocarbon. The alkenyl group can be optionally substituted with one or more halogens selected from the group consisting of F, Cl, Br or I.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. Suitable protecting groups are described, for example, in Greene, et al., "Protective Groups in Organic Synthesis," John Wiley and Sons, Second Edition, 1991, which is incorporated herein by reference in its entirety.

The nucleoside phosphonates of the instant invention can be generally represented by the following structures.

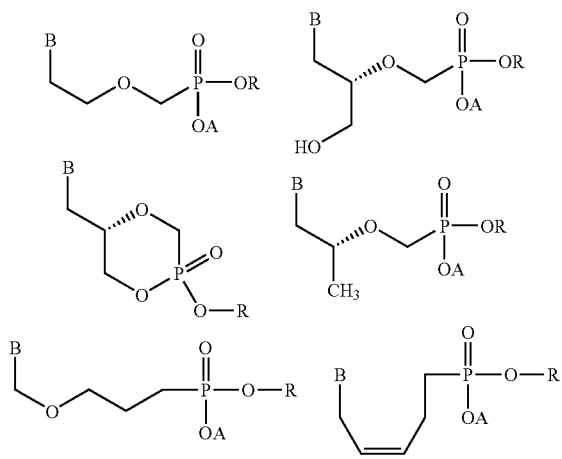

wherein

R is selected from the group consisting of —$R_1$—O—$R_2$, wherein $R_1$ is selected from the group consisting of an optionally substituted $C_1$ to $C_{11}$ alkyl group and $R_2$ is selected from the group consisting of a $C_6$ to $C_{17}$ alkyl group or a $C_6$ to $C_{17}$ alkenyl group;

wherein said $C_6$ to $C_{17}$ alkyl group is substituted with one or more alkyl groups selected from the group including, but not limited to methyl, ethyl, propyl, or cycloalkyl, including, but not limited to cyclopropyl and/or one or more halogens selected from the group consisting of F, Cl, Br and I; and further wherein said $C_6$ to $C_{17}$ alkyl group includes one or more substituents at or near the terminal position of the alkyl group, in particular at the terminal or penultimate position; and wherein said $C_6$ to $C_{17}$ alkenyl group is optionally-substituted with an alkyl group selected from the group including, but not limited to methyl, ethyl, propyl, a cycloalkyl group including, but not limited to cyclopropyl and/or one or more halogens selected from the group consisting of F, Cl, Br and I; and further wherein the said $C_6$ to $C_{17}$ alkenyl group contains one or more double bonds, including a terminal double bond;

B is selected from a purine or pyrimidine base; and

A is a counterion selected from the group including, but not limited to $H^+$, $Li^+$, $Na^+$, $K^+$, $NH_4^+$, tetraalkyl ammonium and other tertiary amine salts including but not limited to triethylamine.

In one embodiment R is selected from the group of compounds having the general structure:

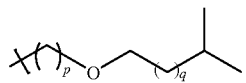

wherein p is selected from 1 to 11 and q is selected from 6 to 17.

In another embodiment R is selected from the group of compounds having the general structure:

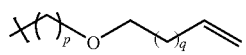

wherein p and q are as defined above.

In yet another embodiment R is selected from the group of compounds having the general structure:

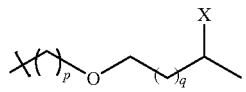

wherein p and q are as defined above and X is a halogen. In preferred embodiments X is F.

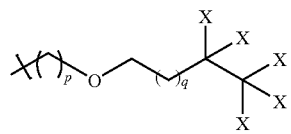

wherein p and q are as defined above and X is independently selected from a halogen. In preferred embodiments X is F.

Figure 2:
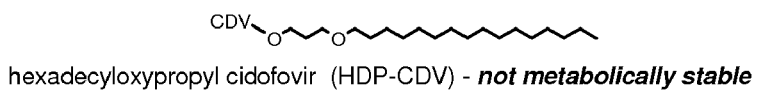
FIG. 2 depicts representative structures of "Metabolism Resistant" lipophilic esters of cidofovir.
Figure 2:
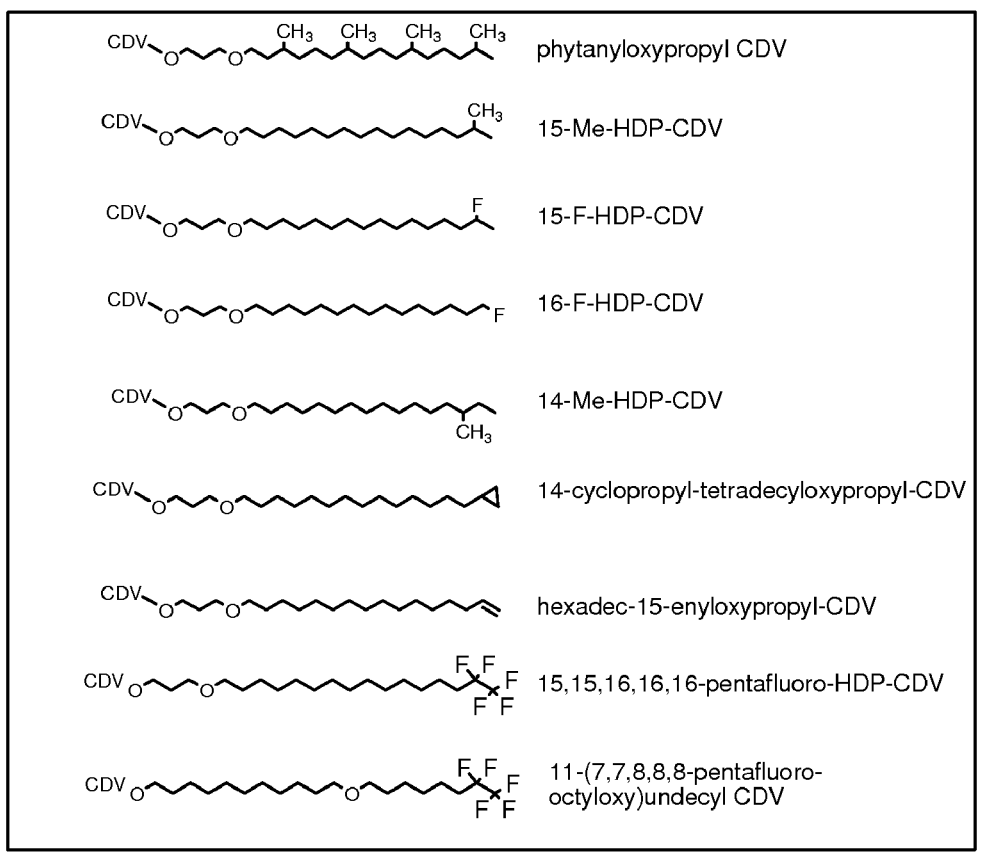

In specific embodiments R is selected from the group consisting of one of the structures set forth in FIG. 2.

In one embodiment of the invention derivatized nucleoside phosphonates are analogs of cyclic cidofovir or cidofovir which can be generally represented by the following structures:

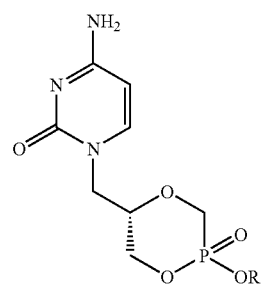

cyclic cidofovir

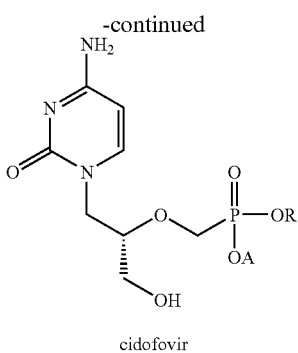

cidofovir wherein R and A are as defined above.

In another embodiment of the invention the derivatized nucleoside phosphonates are analogs of 9-(S)-(3-hydroxy-2-phosphonomethoxypropyl)-adenine ((S)-HMPMA) which can be generally represented by the following structure:

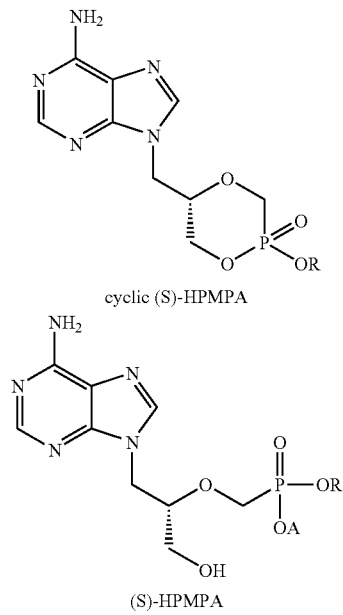

cyclic (S)-HPMPA (S)-HPMPA wherein R and A are as defined above.

Specific analogs of cyclic cidofovir, cidofovir and HPMPA included in the present invention include the following compounds: 3-(12-methyltridecyloxy)propyl cyclic cidofovir, 3-(13-methyltetradecyloxy)propyl cyclic cidofovir, 3-(14-methylpentadecyloxy)propyl cyclic cidofovir, 2-(17-methyloctadecyloxy)ethyl cyclic cidofovir, 3-(15-methylhexadecyloxy)propyl cyclic cidofovir, 3-(15-methylhexadecyloxy)ethyl (S)-cyclic HPMPA, 3-(15-methylhexadecyloxy)propyl (S)-cyclic HPMPA, 2-(17-methyloctadecyloxy)ethyl-(S)-cyclic HPMPA, 3-(12-methyl-tridecyloxy)propyl cidofovir, 3-(13-methyl-tetradecyloxy)propyl cidofovir, 3-(14-methyl-pentadecyloxy)propyl cidofovir, 3-(15-methyl-hexadecyloxy)propyl cidofovir, sodium, 3-(15-methyl-hexadecyloxy) propyl cidofovir, ammonium, 2-(17-methyl-octadecyloxy) ethyl cidofovir, 2-(15-methyl-hexadecyloxy)ethyl cidofovir, 3-(phytanyloxy)propyl cidofovir, 3-(15-methylhexadcey-loxy)ethyl-(S)-HPMPA and 2-(17-methyloctadecyloxy) ethyl-(S)-HPMPA, 3-(hex-dec-15-enyloxy)propyl cidofovir, ammonium, 3-(15-fluorohexadecyloxy) propyl cidofovir, 3-(15-fluorohexadceyloxy)propyl cyclic cidofovir, 3-(15-fluorohexadceyloxy)propyl-(S)-HPMPA, 3-(15-fluorohexa-dceyloxy)propyl-(S)-cyclic HPMPA, 3-(16-fluorohexadecy-loxy)propyl cidofovir, 3-(16-fluorohexadecyloxy)propyl cyclic cidofovir, 3-(16-fluorohexadceyloxy)propyl-(S)-HP-MPA, 3-(16-fluorohexadceyloxy)propyl-(S)-cyclic HPMPA and 11-(7,7,8,8,8-pentafluoro-octyloxy)undecyl-cidofovir, ammonium.

The nucleoside phosphates and analogs thereof of the instant invention can be generally represented by the following structures.

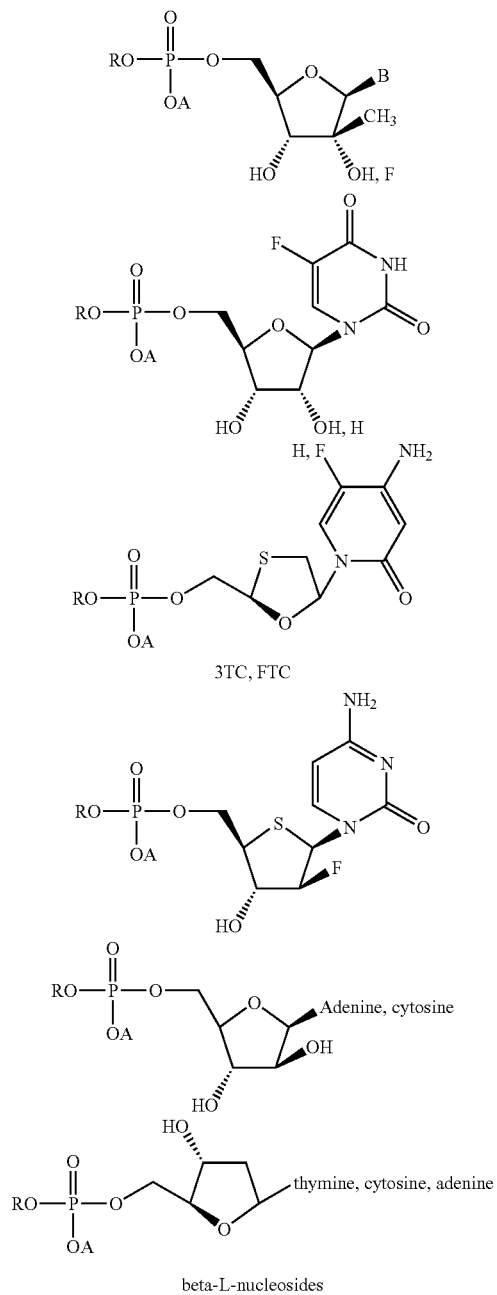

beta-L-nucleosides wherein R is an alkoxyalkyl group having a structure as defined above and B is a substituted or unsubstituted pyrimidine base or their open ring congeners.

Representative examples of nucleosides in this group of compounds include, but are not limited to 2'-C-methyl adenosine, 2'-C-methyl guanosine, 7-deaza-2'-methyl adenosine, 2'-C-methyl cytosine. Other nucleosides and analogs thereof contemplated for use in accordance with this invention following conversion to their alkoxyalkyl 5'-phosphates or their alkoxyalkylglycerol phosphates are set forth in the references cited in Table 2.

Further included are nucleoside analogs with antiviral activity against hepatitis B, which may be converted to their 5'-phosphates, 5'-phosphonates or 5'-methylene phosphonates. Exemplary nucleosides in this class of compounds include, but are not limited to 3TC, FTC, DAPD, L-FMAU, entecavir, telbivudine and various β-L-2'-deoxycytidine, β-L-2'-deoxyadenine and β-L-2'-deoxythymidine analogs described by Bryant et al. ((January 2001) Antimicrob Agents Chemother 45(1):229-235). Phosphates of non-nucleoside antivirals are also subjects of the invention including, but not limited to, zanamivir (Relenza®).

Anticancer agents may also be derivatized according to the method of this invention. Some representative compounds include, but are not limited to 2'-deoxy-2'-fluoromethylene-cytidine (FMdC) and 1-(2-deoxy-2-fluoro-4-thio-β-D-arabinosyl)cytosine (4'-thio-FAC). Other antiproliferative nucleosides may also become more metabolically stable when derivatized according to the invention including, but not limited to Ara-C, Ara-G, 5-fluorouridine, 5-fluoro-deoxyuridine, fludarabine, gemcitabine, decitabine or alkylglycerol phosphate or alkoxyalkyl phosphate esters of taxol. Non-nucleoside cancer agents may be similarly derivatized with the metabolically stable alkoxyalkyl esters of the invention including, but not limited to topotecan by coupling to an available hydroxyl group. Etoposide may be coupled to the metabolically stable alkoxyalkyl esters of the invention by attachment to the phosphate residue of etoposide.

Tables 1 and 2 provide examples of compounds, which may be subjected to the chemical steps of the invention. The references cited in these Tables are hereby incorporated by reference in their entirety.

TABLE 1

References citing illustrative phosphonates, nucleoside phosphonates and nucleoside phosphates for use according to the method of this invention

| DOCUMENT ID | TITLE | AUTHOR (first named) |
|---|---|---|
| U.S. Pat. No. 5,194,654 | Lipid derivatives of phosphonoacids for liposomal incorporation and method of use | Hostetler, K Y |
| U.S. Pat. No. 5,223,263 | Liponucleotide containing liposomes | Hostetler, K Y |
| U.S. Pat. No. 5,411,947 | Method of converting a drug to an orally available form by covalently bonding a lipid to the drug | Hostetler, K Y |
| U.S. Pat. No. 5,463,092 | Lipid derivatives of phosphonoacids for liposomal incorporation and method of use | Hostetler, K Y |
| U.S. Pat. No. 5,484,809 | Prodrugs for oral administration containing taxol or substituted taxol covalently bound to a phospholipid | Hostetler, K Y |
| U.S. Pat. No. 5,696,277 | Antiviral prodrugs | Hostetler, K Y |
| U.S. Pat. No. 5,744,461 | Lipid derivatives of phosphonoacids for liposomal incorporation and methods of use | Hostetler, K Y |
| U.S. Pat. No. 5,744,592 | Lipid prodrugs for oral administration | Hostetler, K Y |
| U.S. Pat. No. 5,817,638 | Antiviral liponucleosides: treatment of hepatitis B | Hostetler, K Y |
| U.S. Pat. No. 5,827,831 | Lipid nucleoside analog prodrugs for oral administration | Hostetler, K Y |
| U.S. Pat. No. 6,002,029 | Antiviral prodrugs | Hostetler, K Y |
| U.S. Pat. No. 6,252,060 | Antiviral liponucleosides: treatment of hepatitis B | Hostetler, K Y |
| U.S. Pat. No. 6,448,392B | Lipid derivatives of antiviral nucleosides: liposomal incorporation and method of use | Hostetler, K Y |
| U.S. Pat. No. 6,599,887B | Methods of treating viral infections using antiviral liponucleotides | Hostetler, K Y |
| U.S. Pat. No. 6,716,825 | Phosphonate compounds | Hostetler, K Y |
| CZ 292199 | O-Phosphonomethyl Choline and Alkyl Esters thereof, process of their preparation and use | Holy, A. (anti-cancer agents) |
| U.S. Pat. No. 6,653,296 | Preparation of Anti-retroviral Enantiomeric nucleotide Analogs | Holy, A. (tenofovir, PMPA) |
| U.S. Pat. No. 6,057,305 | | |
| U.S. Pat. No. 5,977,061 | Acyclic Nucleosides as Virucides and Immunostimulation Suppressants | Holy, A. (HPMPDAP) |
| U.S. Pat. No. 5,733,896 | Preparation of N-(3-fluoro-2-phosphonylmethoxy-propyl)purines and -pyrimidines as antiviral agents | Holy, A. |
| CS 263953 | Method for the Preparation of 9-(S)- and 9-(R,S)-(3-hydroxy-2-phosphonylmethoxypropyl)adenine as virucides | Holy, A. |
| CS 263955 | Method for the preparation of N-[3-hydroxy-2-(phosphonylmethoxy)propyl]purines and -pyrimidines | Holy, A. |
| CS 263956 | Method for the preparation of virucidal 9-(S)-(3-hydroxy-2-phosphonylmethoxypropyl)adenine | Holy, A. |
| U.S. Pat. No. 5,641,763 | Preparation and testing of N-phosphonylmethoxyalkyl derivatives of pyrimidine and purine bases with antiviral activity | Holy, A. (excludes HPMPA, includes PMEG) |
| U.S. Pat. No. 5,869,467 | | |

TABLE 1-continued

References citing illustrative phosphonates, nucleoside phosphonates and
nucleoside phosphates for use according to the method of this invention

| DOCUMENT ID | TITLE | AUTHOR (first named) |
|---|---|---|
| U.S. Pat. No. 4,808,716 | Preparation of 9-[phosphonomethoxy)alkyl]adenines and their use as virucides | Holy, A. (HPMPA) |
| U.S. Pat. No. 4,724,233 | Use of phosphonylmethoxyalkyladenines in the treatment of virus diseases | De Clerq, E. |
| FR 2539132 | Isomeric O-phosphonylmethyl derivatives of enantiomeric and racemic vicinal diols | Holy, A. |
| WO 2004096286 | Preparation of phosphonate prodrugs of antiviral compounds | Boojamara, C. G. |
| US 2004023928 | Phosphonate nucleotide and thiadiazole compounds for the treatment of smallpox | Colacino, J. M. |
| US 2004023921 | Antiviral Phosphonate Nucleotide Analogs | Hong, Z. |
| WO 2003099294 | Improvement in drug selectivity of targeting tissues for therapeutic efficiency | Ubasawa, K. |
| WO 2003090691 | Preparation of phosphonate analogs of HIV protease inhibitors and methods for identifying anti-HIV therapeutic compounds | Birkus, G. |
| WO 2003090690 | Preparation of phosphonate analogs of HIV protease inhibitors with improved cellular accumulation properties | Arimilli, M. N. |
| WO 2003050129 | Use of phosphonate nucleotide analog LY582563 for treating hepatitis B virus infections | Wise, S. D. |
| US 2003109498 | 2-Amino-6-arylthiopurine phosphonate antiviral agents for treatment of drug-resistant virus infections | Yuasa, S. |
| RU 2187509 | Preparation of derivatives of 3'-azido-3'-deoxythymidine 5'-H-phosphonates as antiviral agents | Shirokova, E. A. |
| WO 2003002580 | Preparation of phosphonate-substituted pyrimidine analogs as antiviral agents | Balzarini, J. M. (DAPy) |
| US 644656 U.S. Pat. No. 5,955,610 U.S. Pat. No. 6,005,107 U.S. Pat. No. 6,127,540 | Preparation of antiviral phosphonate nucleotides | Nguyen-Ba, Nghe |
| WO 2002057288 | Preparation of acyclic nucleoside phosphonates as antiviral agents against hepatitis B virus | Choi, J-R. |
| WO 2001064693 | Preparation of phosphonate nucleotide compounds as antiviral agents | Ubasawa, M. |
| WO 2000029414 | Preparation of dialkyl 1-aryl-1-[(2,4-dioxo-1,3-pyrimidin-5-yl)amino]methylphosphonates as antiviral and antimicrobial agents | Tets, v. |
| WO 9962921 | Preparation of antiviral phosphorous derivatives of 4'-thio-5-ethyl-2'-deoxyuridine | Alexandrovna, A. |
| U.S. Pat. No. 5,886,179 U.S. Pat. No. 5,656,745 | Preparation of nucleotide phosphonate ester analogs as antiviral agents | Arimilli, M. N. |
| WO 9319075 | Preparation of purine-substituted phosphonates as antiviral agents | Harnden, M. R. |
| U.S. Pat. No. 5,817,647 U.S. Pat. No. 5,922,696 | Unsaturated phosphonate derivatives of purines and pyrimidines | Casara, P. |
| U.S. Pat. No. 5,532,225 | Preparation of acyclic purine phosphonate nucleotide analogs as antiviral agents | Reist, E. J. |
| U.S. Pat. No. 5,877,166 | Preparation of enantiomerically pure 2-aminopurine phosphonate nucleotide analogs as antiviral agents | Reist, E. J. |
| WO 9842351 | Preparation of difluoronucleoside phosphonic acids as antiviral and antineoplastic agents | Hertel, L. W. |
| WO 9838202 | Preparation of nucleoside phosphonates as antivirals | Rosowsky, A. |
| U.S. Pat. No. 5,717,095 | Preparation of cyclic nucleotide phosphonate esters as virucides | Arimilli, M. N. |
| U.S. Pat. No. 5,650,510 U.S. Pat. No. 5,854,228 | Antiviral phosphonomethoxyalkylpurines and -pyrimidines and their preparation | Webb, R. R. (PMEG) |
| U.S. Pat. No. 5,840,716 | Preparation of acyclic nucleotide phosphonates as virucides | Ubasawa, M. |
| U.S. Pat. No. 5,798,340 U.S. Pat. No. 6,225,460 | Preparation of virucidal nucleotide analogs | Bischofberger, N. W. |
| U.S. Pat. No. 6,197,775 | Preparation of phosphonate acyclic nucleotide derivatives as antiviral agents | Ubasawa, M. |

TABLE 1-continued

References citing illustrative phosphonates, nucleoside phosphonates and
nucleoside phosphates for use according to the method of this invention

| DOCUMENT ID | TITLE | AUTHOR (first named) |
|---|---|---|
| Submitted for publication, 2006 | Synthesis and antiviral evaluation of novel 5-phpsphono-pent-2-en-1-yl nucleosides and their alkoxyalkyl phosphonoesters | Choo, H. et al |
| Antiviral Chemistry and Chemotherapy, 2006, in press | Synthesis and antiviral evaluation of alkoxyalkyl esters of phosphonopropoxymethyl-guanine and phosphonopropoxymethyl-diaminopurine | Ruiz, J et al |

TABLE 2

References citing illustrative analogs of nucleosides, which can be converted
to nucleoside phosphates for use according to the method of this invention

| DOCUMENT ID | TITLE | AUTHOR (first named) |
|---|---|---|
| US 2003/0050229 A1 | Methods and compositions for treating hepatitis C virus | Sommadossi, J-P |
| US 2003/0060400 A1 | Methods and compositions for treating flaviviruses and pestiviruses | LaColla, P. |
| US 2003/0087873 A1 | Modified nucleosides for treatment of viral infections and abnormal cell proliferation | Stuyver, L. |
| US 2004/0063622 A1 | Methods and compositions for treating flaviviruses and pestiviruses | Sommadossi, J-P |
| US 2004/0067877 A1 | 2',3'-dideoxynucleosides for prevention or treatment of flaviviridae infections | Schinazi, R. F. |
| US 2004/0097461 A1 | Methods and compositions for treating hepatitis C virus | Sommadossi, J-P. |
| US 2004/0097462 A1 | Methods and compositions for treating flaviviruses and pestiviruses | Sommadossi, J-P. |
| US 2004/0101535 A1 | Methods and compositions for treating hepatitis C virus | Sommadossi, J-P. |
| US 2004/0254141 A1 | 2'-fluoronucleosides | Schinazi, R. F. |
| US 2003/0008841 A1 | Anti-HCV Nucleoside Derivatives | Devos, R. |
| US 2002/0055483 A1 | 3'- or 2'-hydroxymethyl substituted nucleoside derivatives for treatment of hepatitis virus infections | Watanabe, K. A. |
| US 2002/0147160 A1 | Nucleoside derivatives as inhibitors of RNA-dependent RNA viral polymerase | Bhat, B. |
| U.S. Pat. No. 6,846,810 B2 | Antiviral Nucleoside Derivatives | Martin, J. |
| US 2005/0009775 A1 | Nucleoside compounds in HCV | Howes, P. D. |
| US 2005/0009737 A1 | Modified fluorinated nucleosides | Clark, J. |
| US 20040266722 A1 | 4'-substituted nucleosides as inhibitors of HCV RNA replication | Devos, R. |
| US 2004006358 A1 | Nucleoside Derivatives for Treating Hepatitis C Virus Infection | Roberts, C. |
| US 20040110717 A1 | Nucleoside Derivatives as Inhibitors of RNA-Dependent RNA viral Polymerase | Carroll, S. |
| US 20040121980 A1 | Antiviral Nucleoside Derivatives | Martin, J. |
| US 20040147464 A1 | Nucleoside Derivatives for Treating Hepatitis C Virus Infection | Roberts, C. |
| U.S. Pat. No. 6,784,161 B2 | Method for the Treatment or Prevention of Flavivirus Infections Using Nucleoside Analogues | Ismaili, H. |
| US 20040229840 A1 | Nucleoside Derivatives as Inhibitors of RNA-Dependent RNA Viral Polymerase | Bhat, B. |
| U.S. Pat. No. 6,846,810 B2 | Antiviral Nucleoside Derivatives | Martin, J. |
| US 20050049204 A1 | Compounds for the Treatment of Flaviviridae Infections | Otto, M. |
| US 20050075309 A1 | Purine Nucleoside Analogues for Treating Flaviviridade Including Hepatitis C | Storer, R. |
| US 20050090463 A1 | Nucleoside Compounds for Treating Viral Infections | Roberts, C. |
| US 20050101550 A1 | Nucleoside Compounds for Treating Viral Infections | Roberts, C. |
| US 20050119200 A1 | Nucleoside Derivatives for Treating Hepatitis C Virus Infection | Roberts, C. |
| US 20050124532 A1 | Methods and Compositions for Treating Hepatitis C Virus | Sommadossi, J. |

TABLE 2-continued

References citing illustrative analogs of nucleosides, which can be converted to nucleoside phosphates for use according to the method of this invention

| DOCUMENT ID | TITLE | AUTHOR (first named) |
|---|---|---|
| U.S. Pat. No. 6,911,424 B2 | 2'-Fluoronucleosides | Schinazi, R. |
| US 20050215511 A1 | Nucleoside Compounds for Treating Viral Infections | Roberts, C. |
| US 20050272676 A1 | Nucleoside Derivatives as Inhibitors of RNA-Dependent RNA viral Polymerase | Bhat, B. |
| US 20060040890 A1 | Anti-Viral Nucleosides | Martin, J. |

Compounds of the instant invention can be administered orally in the form of tablets, capsules, solutions, emulsions or suspensions, inhaled liquid or solid particles, microencapsulated particles, as a spray, through the skin by an appliance such as a transdermal patch, or rectally, for example, in the form of suppositories. The lipophilic prodrug derivatives of the invention are particularly well suited for transdermal absorption administration and delivery systems and may also be used in toothpaste. Administration can also take place parenterally in the form of injectable solutions.

The compositions may be prepared in conventional forms, for example, capsules, tablets, aerosols, solutions, suspensions, or together with carriers for topical applications. Pharmaceutical formulations containing compounds of this invention can be prepared by conventional techniques, e.g., as described in *Remington's Pharmaceutical Sciences*, 1985.

The pharmaceutical carrier or diluent employed may be a conventional solid or liquid carrier. Examples of solid carriers are lactose, sucrose, talc, gelatin, agar, pectin, acacia, magnesium stearate, stearic acid, or lower alkyl ethers of cellulose. Examples of liquid carriers are syrup, peanut oil, olive oil, phospholipids, fatty acids, fatty acid amines, polyoxyethylene or water. The carrier or diluent may include any sustained release material known in the art, such as glyceryl monostearate or distearate, alone or mixed with a wax.

If a solid carrier is used for oral administration, the preparation may be tabletted or placed in a hard gelatin capsule in powder or pellet form. The amount of solid carrier will vary widely, but will usually be from about 25 mg to about 1 g. If a liquid carrier is used, the preparation may be in the form of a syrup, emulsion, soft gelatin capsule, or sterile injectable liquid such as an aqueous or non-aqueous liquid suspension or solution.

Tablets are prepared by mixing the active ingredient (that is, one or more compounds of the invention), with pharmaceutically inert, inorganic or organic carrier, diluents, and/or excipients. Examples of such excipients which can be used for tablets are lactose, maize, starch or derivatives thereof, talc, stearic acid or salts thereof. Examples of suitable excipients for gelatin capsules are vegetable oils, waxes, fats, semisolid, and liquid polyols.

For nasal administration, the preparation may contain a compound of the invention dissolved or suspended in a liquid carrier, in particular, an aqueous carrier, for aerosol application. The carrier may contain solubilizing agents such as propylene glycol, surfactants, absorption enhancers such as lecithin or cyclodextrin, or preservatives.

Pharmaceutical compositions of this invention for parenteral injection comprise pharmaceutically acceptable sterile aqueous or non-aqueous liquids, dispersions, suspensions or emulsions as well as sterile powders for reconstitution into sterile injectable solutions or dispersions just prior to use.

Suitable excipients for the preparation of solutions and syrups are water, polyols, sucrose, invert sugar, glucose, and the like. Suitable excipients for the preparation of injectable solutions are water, alcohols, polyols, glycerol, vegetable oils, and the like.

The pharmaceutical products can additionally contain any of a variety of added components, such as, for example, preservatives, solubilizers, stabilizers, wetting agents, emulsifiers, sweeteners, colorants, flavorings, buffers, coating agents, antioxidants, diluents, and the like.

Optionally, the pharmaceutical compositions of the invention may comprise a compound according to the general formula combined with one or more compounds exhibiting a different activity, for example, an antibiotic or other pharmacologically active material. Such combinations are within the scope of the invention.

This invention provides methods of treating disorders related to viral infections, inappropriate cell proliferation, and the like. The methods particularly comprise administering to a host in need thereof a therapeutically effective amount of the prodrugs of this invention. Thus, in one aspect of the invention there are provided methods for treating disorders caused by viral infections. Indications appropriate to such treatment include susceptible viruses including, but are not limited to human immunodeficiency virus (HIV), influenza, herpes simplex virus (HSV), human herpes virus 6 and 8, cytomegalovirus (CMV), hepatitis B and C virus, Epstein-Barr virus (EBV), varicella zoster virus, and diseases caused by orthopox viruses (e.g., variola major and minor, vaccinia, smallpox, cowpox, camelpox, monkeypox, and the like), ebola virus, papilloma virus, and the like, lymphomas, hematological disorders such as leukemia, and the like, and cancers caused by viruses such as cervical cancer which is caused, in most cases, by the high risk subtypes of human papilloma virus.

In yet another aspect of the invention, there are provided methods for treating disorders caused by inappropriate cell proliferation, e.g. cancers, such as melanoma, lung cancers, pancreatic cancer, stomach, colon and rectal cancers, prostate and breast cancer, the leukemias and lymphomas, and the like. Anti-cancer compounds which can be converted to their nucleotide phosphonates or nucleoside-5'-phosphates for use as compounds of this invention include, but are not limited to, cytarabine (ara-C), fluorouridine, fluorodeoxyuridine (floxuridine), gemcitibine, decitabine, cladribine, fludarabine, pentostatin (2'-deoxycoformycin), 6-mercaptopurine and 6-thioguanine and substituted or unsubstituted ara-adenosine (ara-A), ara-guanosine (ara-G), and ara-uridine (ara-U). Anticancer compounds of the invention may be used alone or in combination with other antimetabolites or with other classes of anticancer drugs such as alkaloids, topoisomerase inhibitors, alkylating agents, antitumor antibiotics, and the like.

The prodrugs of the invention can be administered orally, parenterally, topically, rectally, and through other routes, with appropriate dosage units, as desired.

As used herein, the term "parenteral" refers to subcutaneous, intravenous, intra-arterial, intramuscular or intravitaeal injection, or infusion techniques.

The term "topically" encompasses administration rectally and by inhalation spray, as well as the more common routes of the skin and mucous membranes of the mouth and nose and in toothpaste.

"Therapeutic" as used herein, includes treatment and/or prophylaxis. When used, therapeutic refers to humans as well as other animals.

"Pharmaceutically or therapeutically effective dose or amount" refers to a dosage level sufficient to induce a desired biological result. That result may be the alleviation of the signs, symptoms or causes of a disease or any other alteration of a biological system that is desired.

A "host" or "patient" is a living subject, human or animal, into which the compositions described herein are administered.

With respect to disorders associated with viral infections or inappropriate cell proliferation, e.g., cancer, the "effective amount" is determined with reference to the recommended dosages of the antiviral or anticancer parent compound. The selected dosage will vary depending on the activity of the selected compound, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient will depend on a variety of factors, including the body weight, general health, diet, time, and route of administration and combination with other drugs, and the severity of the disease being treated.

Generally, the compounds of the present invention are dispensed in unit dosage form comprising 1% to 100% of active ingredient. The range of therapeutic dosage is from about 0.01 to about 1,000 mg/kg/day with from about 0.10 mg/kg/day to 100 mg/kg/day being preferred, when administered to patients, e.g., humans, as a drug. Actual dosage levels of active ingredients in the pharmaceutical compositions of this invention may be varied so as to administer an amount of the active compound(s) that is effective to achieve the desired therapeutic response for a particular patient.

Compounds of the invention can be prepared in a variety of ways, as generally depicted in Schemes 3 to 7 in Examples 1-9. The general phosphonate esterification methods described below are provided for illustrative purposes only and are not to be construed as limiting this invention in any manner. Indeed, several methods have been developed for direct condensation of phosphonic acids with alcohols (see, for example, R. C. Larock, *Comprehensive Organic Transformations*, VCH, New York, 1989, p. 966 and references cited therein). Isolation and purification of the compounds and intermediates described in the examples can be effected, if desired, by any suitable separation or purification procedure such as, for example, filtration, extraction, crystallization, flash column chromatography, thin-layer chromatography, distillation or a combination of these procedures. Specific illustrations of suitable separation and isolation procedures are in the examples below. Other equivalent separation and isolation procedures can of course, also be used.

Example 1 (Scheme 1) outlines a general method for the synthesis of branched alkoxyalkanols having the general formula:

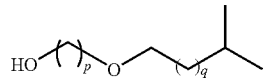

wherein p and q are as defined above.

Example 2 (Scheme 2) outlines a general method for the synthesis of branched methylalkoxyalkyl esters from cyclic phosphonates. Cyclic cidofovir was used in this Example for purposes of illustration, however this method can be extended to the use of virtually any cyclic phosphonate of interest. The following compounds were prepared using the general methods set forth in Examples 1 and 2: 3-(12-methyl-tridecyloxy) propyl cidofovir, 3-(13-methyl-tetradecyloxy)propyl cidofovir, 3-(14-methyl-pentadecyloxy)propyl cidofovir, 3-(15-methyl-hexadecyloxy)propyl cidofovir, sodium, 2-(17-methyl-octadecyloxy)ethyl cidofovir, 2-(15-methyl-hexadecyloxy)ethyl cidofovir, 3-(15-methylhexadceyloxy) ethyl-(S)-HPMPA, and 2-(17-methyloctadecyloxy)ethyl-(S)-HPMPA.

Examples 3 and 4 describe the synthesis of two specific branched alkoxyalkyl esters, namely 3-(phytanyloxy)propyl cidofovir and 15-methylhexadecyloxypropyl cidofovir (15-Me HDP-CDV), ammonium, using slight variations of the methods described in Examples 1 and 2.

Example 5 (Scheme 4) describes a general method for the synthesis of the branched methylalkoxyalkyl esters of the instant invention from p-toluenesulfonyloxymethyl phosphonates. The synthesis of the branched methylalkoxyalkyl ester 3-(15-methyl-hexadecyloxy)propyl (S)-9-[3-trityloxy-2-(phosphonomethoxy)propyl]-N⁶-trityl-adenine, was described for purposes of illustration.

Example 6 (Scheme 5) outlines a general method for the synthesis of alkenyloxyalkyl esters having a terminal double bond. The nucleoside phosphonate cidofovir was used for purposes of illustration resulting in the synthesis of compound 26, hexadec-15-enyl-oxypropyl-cidofovir.

Examples 7-9 (Schemes 6-8) outline general methods for the synthesis of various halogenated alkoxyalkyl esters using CDV and HPMPA for purposes of illustration. Synthesis of the following compounds are exemplified: 3-(15-fluorohexadecyloxy)propyl cidofovir, 3-(15-fluorohexadecyloxy)propyl cyclic cidofovir, 3-(15-fluorohexadecyloxy)propyl-(S)-HPMPA, 3-(15-fluorohexadecyloxy)propyl-(S)-cyclic HPMPA, 3-(16-fluorohexadecyloxy)propyl cidofovir, 3-(16-fluorohexadecyloxy)propyl cyclic cidofovir, 3-(16-fluorohexadecyloxy)propyl-(S)-HPMPA, 3-(16-fluorohexadecyloxy)propyl-(S)-cyclic HPMPA and 11-(7,7,8,8,8-pentafluoro-octyloxy)undecyl cidofovir.

Examples 10-12 illustrate the antiviral activity representative penultimate branched methyl alkoxyalkyl esters of CDV and HPMPA. The results are set forth in Tables 3-6. As can be seen in Tables 4 and 5 penultimate branched chain analogs of (S)-HPMPA were highly active against vaccinia and cowpox in vitro and penultimate branched chain alkoxyalkyl cidofovir esters were effective against ectromelia virus in vitro at submicromolar EC50s. As can be seen in Table 6, the branch chain analogs of (S)-HPMPA and CDV were all fully protective against death from lethal poxvirus infection at doses of 5 mg/kg/day or greater. 15M-HDP-(S)-HPMPA appeared to be more active than HDP-(S)-HPMPA.

Figure 3:
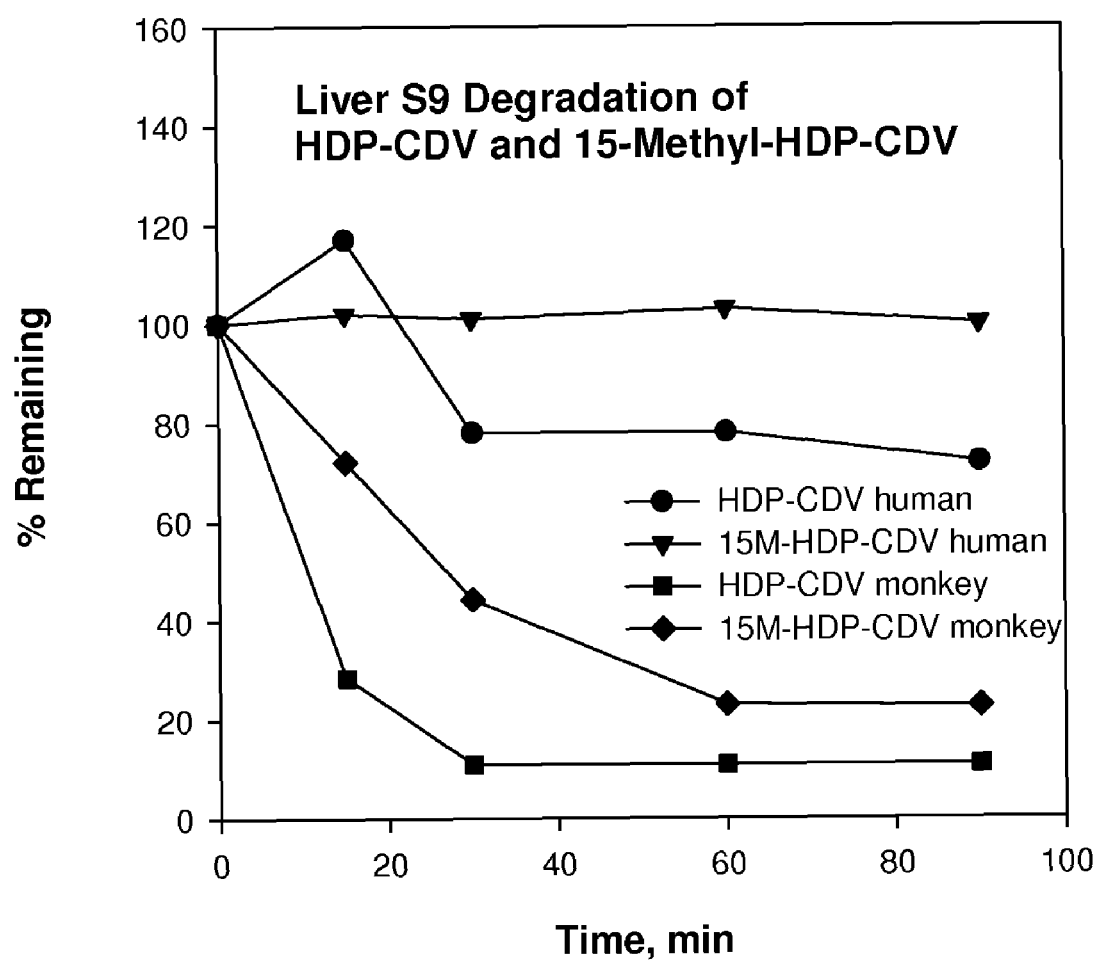
FIG. 3 depicts a graph of the % of drug remaining versus time for HDP-CDV and 15-methyl-HDP-CDV (15M-HDP-CDV). This figure illustrates that the degradation of branched alkoxyalkyl ester derivative 15M-HDP-CDV by monkey liver fractions is markedly slower than that of the straight chain alkoxyalkyl ester derivative HDP-CDV. The methods are described in Example 13.

The stability of the compounds of the invention is illustrated in Example 13, the data for which is set forth in FIG. 3. FIG. 3 depicts a graph of the % of drug remaining versus time for HDP-CDV and 15-methyl-HDP-CDV (15M-HDP-CDV) after incubation for various times as indicated in the presence of liver S9 preparations. This figure illustrates that the degradation of branched alkoxyalkyl ester derivative 15M-HDP-CDV by monkey liver and human liver S9 fractions is markedly slower than that of the straight chain alkoxyalkyl ester derivative HDP-CDV. Thus, changes in the alkyl chain to mimic the features of phytanic acid (3,7,11,15-tetramethyl-hexadecanoic acid) slow ω oxidation of the 16th carbon. Although, the phytantyl derivative illustrated in Example 13 contains 4 methyl groups it is also sufficient to introduce alkyl substituents or halogens at the penultimate carbon as in the hexadecyl moiety of HDP-CDV (15-methyl-hexadecyloxypropyl-cidofovir, 15M-HDP-CDV). Alternatively, terminal fluorines, cyclopropyl, alkene groups also suffice to increase metabolic stability as described in detail above.

EXAMPLES

The following examples are provided for illustrative purposes only and are not intended to limit the scope of the invention.

General Procedures. $^1$H NMR spectra were recorded on a Varian HG spectrophotometer operating at 300 MHz and are reported in units of ppm relative to internal tetramethylsilane at 0.00 ppm. Analtech silica gel-GF (250 micron) plates were used for thin layer chromatography (TLC). The products were visualized with UV light, phospray (Supelco; Bellefonte, Pa., USA) and charring. Flash chromatography was performed with silica gel (E. Merck silica gel 60, 230-400 mesh) or with a CombiFlash system (Teledyne Isco, Lincoln, Nebr.). Mass spectra showing the presence of a molecular ion were obtained using electrospray ionization (MS-ESI) in both positive and negative modes.

Example 1

Preparation of Branched alkoxyalkanols

A general method for the synthesis of branched alkoxyalkanols (6) is illustrated in Scheme 1.

Scheme 1

| Compound | n | m | p |
|---|---|---|---|
| 12-methyltridecyloxypropan-1-ol | 1 | 7 | 3 |
| 13-methyltetradecyloxypropan-1-ol | 1 | 8 | 3 |
| 14-methylpentadecyloxypropan-1-ol | 3 | 7 | 3 |
| 15-methylhexadecyloxypropan-1-ol | 1 | 10 | 3 |
| 17-methyloctadecyloxyethan-1-ol | 3 | 10 | 2 |
| 15-methylhexadecyloxyethan-1-ol | 1 | 10 | 2 |

Reagents: a) magnesium, THF; b) Li$_2$CuCl$_4$, THF; c) methanesulfonyl chloride, triethylamine, CH$_2$Cl$_2$; d) 1,2-ethanediol or 1,3-propanediol, NaH, N,N-DMF Preparation of branched methylalkanols (4). With reference to Scheme 1, branched methylalkanols were synthesized from bromoalkanols (3) and branched methyl bromoalkanes (1). The chain elongation procedures are described by Fouquet et al. (Fouquet and Sclosser (1974) Angew. Chem. Int. Ed. Engl. 13:82-83).

General procedure. A dry THF solution of alkylmagnesium bromide (2) was prepared from branched methyl alkyl bromide (1, 94.2 mmol) and magnesium (113 mmol) in dry THF (90 mL). To a stirred and cooled solution of bromoalkanol (3, 17.3 mmol) in dry THF (50 mL) was added the resulting Grignard reagent, followed by a solution of Li$_2$CuCl$_4$ (0.12 M in dry THF, 8.0 mL, 0.96 mmol) at −78° C. under N$_2$ atmosphere. The resulting mixture was allowed to warm to room temperature while stirring overnight. After the reaction mixture had been quenched with saturated aq. NH$_4$Cl, it was extracted with ethyl acetate. The extract was successively washed with water, saturated NaHCO$_3$ and brine, dried with MgSO$_4$, and concentrated under reduced pressure. The residue was purified by flash column chromatography (10% ethyl acetate/hexanes) to provide the branched methylalkanols (4).

The following compounds were prepared using this general procedure.

12-methyltridecan-1-ol was prepared from 9-bromononan-1-ol and 3-methylbutylbromide in 51% yield. The $^1$H NMR and MS-ESI data matched those reported by Yuasa et al. (Yuasa and Tsuruta (2004) Flavour and Fragrance Journal 19:199-204).

13-methyltetradecan-1-ol was prepared from 10-bromodecanol and 3-methylbutylbromide in 62% yield. The $^1$H NMR and MS-ESI data matched those reported by Yuasa et al. (Yuasa and Tsuruta (2004) Flavour and Fragrance Journal 19:199-204).

14-methylpentadecan-1-ol was prepared from 9-bromononanol and 5-methylhexylbromide in 55% yield. The $^1$H NMR and MS-ESI data matched those reported by Yuasa et al. (Yuasa and Tsuruta (2004) Flavour and Fragrance Journal 19:199-204).

15-methylhexadecan-1-ol was prepared from 12-bromo-1-dodecanol and 3-methylbutylbromide. The $^1$H NMR was identical to that reported by Masuda et al. ((2002) Biosci. Biotech. Biochem. 66:1531-1537).

17-methyloctadecan-1-ol was prepared from 12-bromo-1-dodecanol and 5-methylhexylbromide in 44% yield. $^1$H NMR δ 0.86 (6H), 1.10-1.40 (32H), 3.64 (2H).

Preparation of branched alkoxyalkanols (6). With reference to Scheme 1, branched alkoxyalkanols were prepared by conversion of the branched methyl alkanols (4) to the corresponding methanesulfonate derivatives (5), followed by reaction with either 1,3-propanediol or 1,2-ethanediol.

General procedure for preparation of methanesulfonates. To a solution of alkanol 4 (100 mmol) and triethylamine (15.2 g, 150 mmol) in CH$_2$Cl$_2$ (100 mL) was added methanesulfonyl chloride (15 g, 130 mmol) at 0° C. The reaction mixture was stirred overnight then poured into ice water and extracted with diethyl ether. The extract was washed with saturated aq. NaHCO$_3$ and brine, dried with MgSO$_4$ and concentrated under reduced pressure to give the branched methyl alkylmethanesulfonate 5 in 79-89% yield. The compound was employed in the next step without further purification.

General procedure for preparation of alkoxyalkanols. 1,3-propanediol or 1,2-ethanediol (10 mmol) was added carefully to a suspension of sodium hydride (2 mmol) in dry N,N-DMF and stirred for 30 min. To the mixture was then added the branched methyl alkylmethanesulfonate (5, 1 mmol) in dry THF. The mixture was heated to 60° C. for 4 h, and then cooled to room temperature. After the mixture had been added to ice water it was extracted with ethyl acetate, washed with brine and concentrated under reduced pressure. The residue was purified by flash chromatography (20% ethyl acetate/hexanes) to give the branched methylalkoxyalkanols (6).

The following compounds were prepared using these procedures.

3-(12-methyltridecyloxy)propan-1-ol,
3-(13-methyltetradecyloxy)propan-1-ol,
3-(14-methylpentadecyloxy)propan-1-ol,
3-(15-methylhexadecyloxy)propan-1-ol $^1$H NMR δ 0.86 (d, 6H), 1.15 (m, 1H), 1.25 (br s, 26H), 1.60-1.46 (m, 3H), 1.83 (qt, 2H), 3.43 (t, 2H), 3.61 (t, 2H), 3.78 (t, 2H). MS-ESI (m/z) 315.33 (MH)$^+$
2-(15-methylhexadecyloxy)ethan-1-ol
2-(17-methyloctadecyloxy)ethan-1-ol Example 2

Preparation of Branched methylalkoxyalkyl esters from cyclic phosphonates

Branched methylalkoxyalkyl esters were prepared from cyclic phosphonates as shown in Scheme 2 using cyclic cidofovir for purposes of illustration. Briefly, the cyclic phosphonates were coupled to branched methylalkoxyalkanols using the Mitsunobu reaction as described by Wan et al. ((2005) Antimicrobial Agents and Chemotherapy 49:656-662) to form the cyclic diesters which were then hydrolyzed to form the branched methylalkoxyalkyl esters.

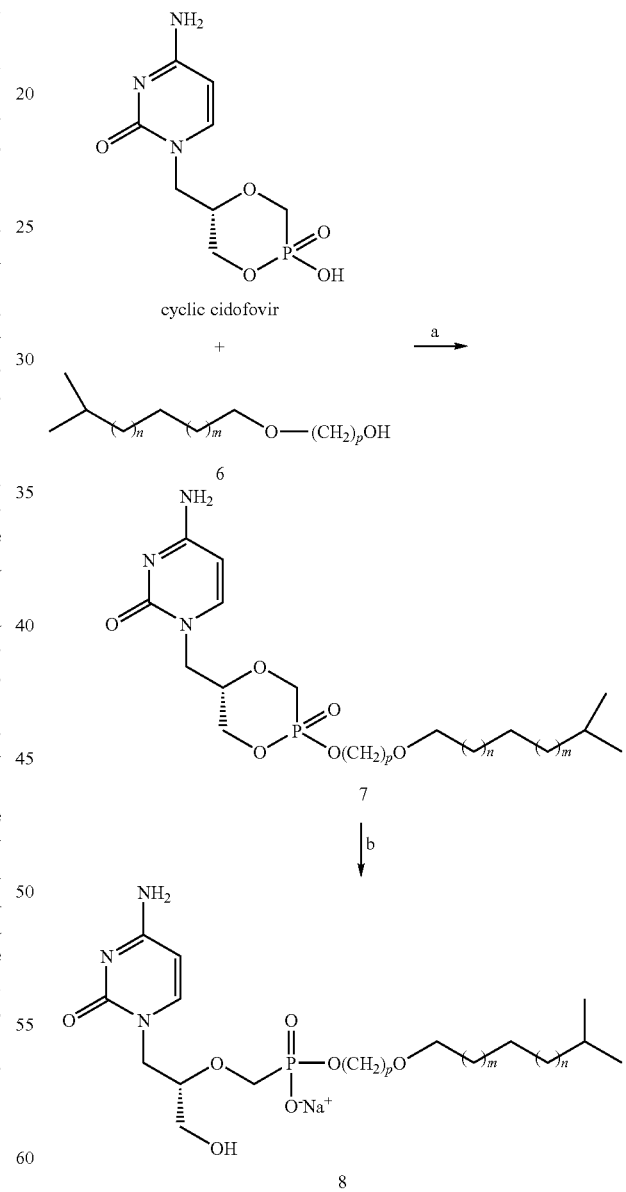

Reagents: a) triphenylphosphine, diisopropyl azodicarboxylate, N,N-DMF; b) 2M aq. NaOH, 80° C.

General procedure for preparation of cyclic diesters (illustrated by compound L. Anhydrous cyclic cidofovir or cyclic (S)-HPMPA (10 mmol), an alkoxyalkanol (6) (20 mmol) and triphenylphosphine (20 mmol) were dissolved or suspended in anhydrous N,N-dimethylformamide (15 mL) and stirred vigorously under a nitrogen atmosphere. Diisopropyl azodicarboxylate (20 mmol) was added in three portions over 15 min and then the mixture was stirred overnight at room temperature. The solvent was then evaporated under vacuum, and the residue was purified by flash column chromatography (15% EtOH/CH$_2$Cl$_2$). The products were finally recrystallized from p-dioxane. The coupled products were equimolar mixtures of the axial and equatorial diastereomers.

The following compounds were prepared:
3-(12-methyltridecyloxy)propyl cyclic cidofovir
3-(13-methyltetradecyloxy)propyl cyclic cidofovir
3-(14-methylpentadecyloxy)propyl cyclic cidofovir
2-(17-methyloctadecyloxy)ethyl cyclic cidofovir
3-(15-methylhexadecyloxy)propyl cyclic cidofovir MS-ESI (m/z) 558.54 (MH)$^+$
3-(15-methylhexadecyloxy)ethyl (S)-cyclic HPMPA
3-(15-methylhexadecyloxy)propyl (S)-cyclic HPMPA MS-ESI (m/z) 582.37 (MH)$^+$
2-(17-methyloctadecyloxy)ethyl-(S)-cyclic HPMPA MS-ESI (m/z) 596.32 (MH)$^+$ General procedure for preparation of branched methylalkoxyalkyl esters (illustrated by compound 8). The branched methyl alkoxyalkyl esters of cyclic cidofovir (7) or cyclic (S)-HPMPA were suspended in 2 M NaOH (25 mL/mmol), heated to 80° C. and stirred for 1 h, during which time the mixtures became clear. After hydrolysis, the solutions were cooled to 25° C. and acidified with glacial acetic acid to approximately pH 5. The resulting precipitates were collected by vacuum filtration and dried under reduced pressure. The crude products were purified either by flash column chromatography (20% MeOH/CH$_2$Cl$_2$) or recrystallized from ethanol.

The following compounds were prepared:
3-(12-methyltridecyloxy)propyl cidofovir
3-(13-methyltetradecyloxy)propyl cidofovir
3-(14-methylpentadecyloxy)propyl cidofovir
3-(15-methylhexadecyloxy)propyl cidofovir, sodium MS-ESI (m/z) 598.36 (M+Na)$^+$
2-(17-methyloctadecyloxy)ethyl cidofovir
2-(15-methyl-hexadecyloxy)ethyl cidofovir
3-(15-methylhexadceyloxy)ethyl (S)-HPMPA
2-(17-methyloctadecyloxy)ethyl (S)-HPMPA MS-ESI (m/z) 614.30 (MH)$^+$.

Example 3

Preparation of 3-(phytanyloxy)propyl cidofovir 3-(Phytanyloxy)propyl cidofovir was prepared using slight modifications of the general methods set forth in Examples 1 and 2 as specifically set forth below.

Preparation of phytanol. Phytol (2.0 g, 6.7 mmol) was dissolved in ethanol, rhodium 5% on alumina was added and mixture was placed under H$_2$ 60 psi and shaken overnight. The reaction mixture was filtered and evaporated to give the desired compound as an oil (2.0 g, 100% yield).

Preparation of phytanylmethanesulfonate. Phytanol (2.0 g, 6.7 mmol) was dissolved in pyridine and cooled to 0° C. Methanesulfonyl chloride (1.15 g, 10 mmol) was added and the reaction mixture was stirred for 4 h, after which the mixture was added to ice water and extracted with ether. The ether layer was evaporated to provide a light brown oil (1.5 g) that was used in the next step without further purification.

Preparation of 3-(phytanyloxy)propan-1-ol. Sodium hydride was added carefully to a solution of 1,3-propanediol (7.6 g, 100 mmol) in anhydrous N,N-DMF (30 mL). Phytanylmethanesulfonate (1.5 g, 4 mmol) was added and the mixture was heated to 60° C. and stirred for 4 h. The reaction mixture was then poured into ice/H$_2$O, extracted with dichloromethane, dried over MgSO$_4$ and evaporated. The residue was purified by flash column chromatography using 20% ethyl acetate/hexanes to give 3-(phytanyloxy)propan-1-ol (1.25 g, 87% yield)

Preparation of 3-(phytanyloxy)propyl cyclic cidofovir. To a stirred mixture of triphenylphosphine, (524 mg, 2 mmol) cyclic cidofovir (anhydrous, 800 mg, 3 mmol) and phytanyloxypropanol (500 mg, 1.4 mmol) was added diisopropyl azodicarboxylate (404 mg, 2 mmol). The mixture was then stirred overnight at room temperature. Solids were removed by filtration and then the filtrate was concentrated and the residue purified by flash column chromatography. Elution with 10-15% EtOH/dichloromethane afforded the cyclic ester (660 mg, 78%)

Preparation of 3-(phytanyloxy)propyl cidofovir. Phytanyloxypropyl cyclic cidofovir was hydrolyzed as described in Example 2 to provide the target compound.

Example 4

Preparation of 15-methylhexadecyloxypropyl cidofovir (15-Me HDP-CDV)

15-Me HDP-CDV, ammonium (16) was prepared using slight modifications of the general methods set forth in Examples 1 and 2 as specifically set forth below and outlined in Scheme 3.

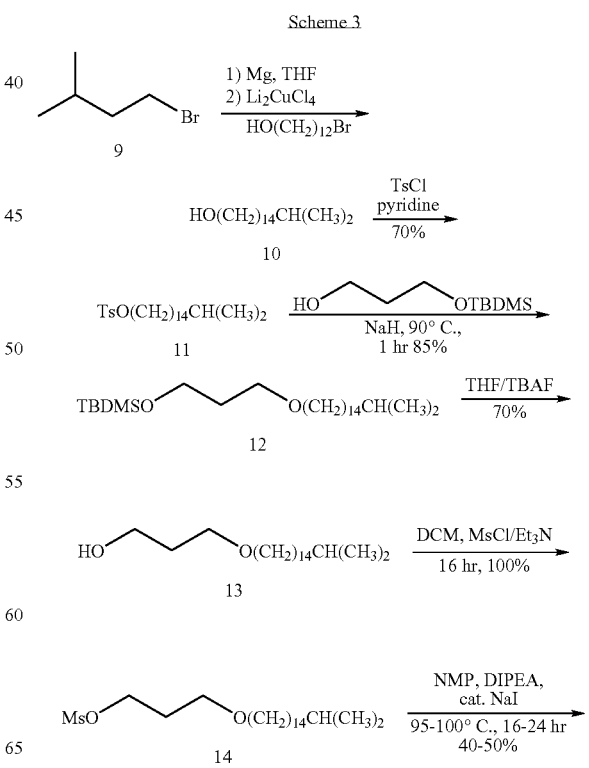

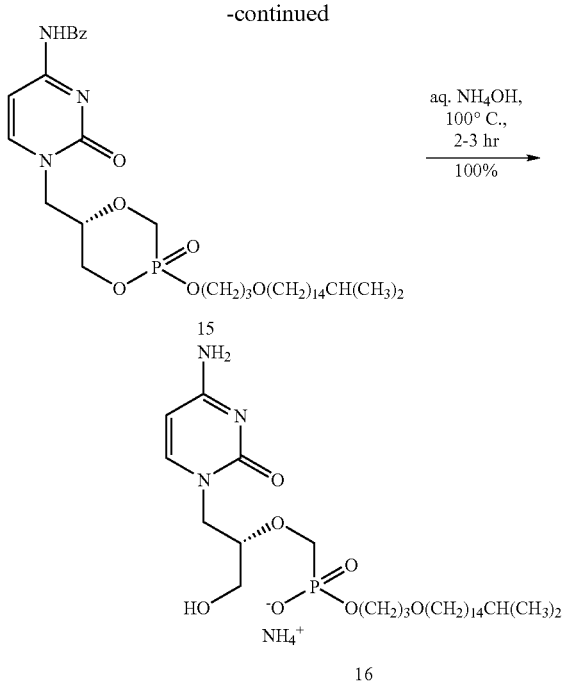

15-Methylhexadecan-1-ol (10). Into a clean flame dried and Ar flushed 500 mL RBF was added 5 g (33 mmol) of commercially available 9. To this was added 40 mL of anhydrous THF and 970 mg (40 mmol) of Mg turnings, a pellet of I$_2$ was added to accelerate the reaction. The reaction mixture was refluxed for 2 hrs. It was then cooled to room temperature and further to −78° C. To this was added 1.6 g (6.0 mmol) of 12-bromo-1-dodecanol in 10 mL of anhydrous THF followed by addition of 3.3 mL (0.33 mmol) of lithium cuprate. The resulting mixture was allowed to warm to room temperature while stirring overnight followed by quenching with saturated aq. NH$_4$Cl and extracted with EtOAc (3×). The combined EtOAc layer was then successively washed with water, saturated aq. NaHCO$_3$ and brine, dried over MgSO$_4$ and the solvents evaporated under reduced pressure. The residue was then purified by combiflash using hexane/EtOAc as eluent to furnish 1.07 g of the compound 10 as a white solid in 65-70% yield.

15-Methylhexadecyl-1-tosylate (11). 22 g (86 mmol) of 10 was dissolved in 200 mL of dry DCM and 14 mL (100 mmol) of Et$_3$N was added. The solution was cooled to 0° C. followed by addition of 19 g (100 mmol) of TsCl. The reaction mixture was then stirred for 6 hrs at room temperature and washed with saturated solution of aq. NaHCO$_3$, the organic layer was then dried over MgSO$_4$ and the solvent was evaporated under reduced pressure. The crude product was then purified by combiflash using hexane/EtOAc as eluent and recrystallized over hexanes at −20° C. overnight to provide 25 g of 11 as white crystals in 70% yield.

tert-Butyldimethyl-3-(15-methylhexadecyloxy)propoxysilane (12). Into a clean flame dried and Ar flushed 2 L RBF was added 22.5 ml (105 mmol) of commercially available 3-tert-butyldimethylsilyloxy propanol and 200 mL of anhydrous DMF was added. The mixture was cooled to 0° C. and 5.0 g of NaH was added slowly. After complete addition the reaction mixture was stirred at room temperature for 30 minutes and cooled to 0° C. 27 g (65.7 mmol) of 11 was then slowly added to the reaction with vigorous stirring. After complete addition the reaction mixture was heated at 80° C. for 2 hrs at which time the TLC showed complete consumption of 11. The reaction was then cooled to room temperature and quenched with dropwise addition of saturated aq. NH$_4$Cl. 200 mL of water was added and the target product was extracted with EtOAc (3×), the combined organic layer was successively washed with water (3×), brine (1×) and dried over MgSO$_4$. The solvent was evaporated under reduced pressure and the residue was purified by combiflash using hexane/ethyl acetate as an eluent to furnish 23 g of 12 as colorless oil in 85% yield.

3-(15-methylhexadecyloxypropan-1-ol (13). To 23 g (54 mmol) of 12 was added 216 mL of a 1 M solution of TBAF in THF and the reaction was stirred for 16 hrs at room temperature. The reaction mixture was then quenched with saturated solution of aq. NH$_4$Cl and the THF was evaporated under reduced pressure. The aq. solution was then diluted with 200 mL of water and the target product was extracted with Et$_2$O (3×), the combined organic layer was then washed with brine (1×), dried over MgSO$_4$ and the solvent was removed under reduced pressure. The crude product was then purified by combiflash using hexane/ethyl acetate as eluent to furnish 11.5 g of compound 13 in 70% yield as yellow oil.

Methanesulfonic acid-3-(15-methylhexadecyloxy)propyl ester (14). To 11 g (35 mmol) of 13 was added 25 mL of DCM and 7.3 mL (53 mmol) of Et$_3$N and the mixture was cooled to 0° C. MsCl 3.0 mL (38.5 mmol) and a catalytic amount of DMAP was then added dropwise and the reaction was stirred at room temperature overnight. The reaction mixture was then diluted with 50 mL of DCM and washed successively with saturated solution of aq. NaHCO$_3$ (1×), water (1×) and brine (1×), dried over MgSO$_4$ and the solvent was evaporated under reduced pressure. The crude product was then purified by combiflash using hexane/ethyl acetate as eluent to furnish 13 g of product 14 in quantitative yield.

Reaction of 14 with Bz-c-CDV. 2.4 g (6.6 mmol) of Bz-c-CDV was dissolved in 10 mL of NMP and 1.7 mL (10 mmol) of DIPEA was added to it followed by 13 g (33 mmol) of 14. The reaction mixture was heated to 95-100° C. for 16 hrs at which time TLC showed product together with some Bz-c-CDV. The reaction was allowed to proceed for an additional 8-9 hrs, at which time TLC showed that the reaction had not proceeded much further. At this time, the reaction mixture was cooled to room temperature and the solvent was evaporated under high vacuum. The residue was purified by combiflash using chloroform/MeOH as eluent to furnish 1.8 g of 15 as yellow oil in 42% yield.

Deprotection and hydrolysis of (15). To 1.7 g (2.56 mmol) of 15 was added 30 mL of concentrated NH$_4$OH and the sealed tube was heated at 95° C. for 2-3 hrs at which time the solution turned clear. The reaction mixture was then cooled and the TLC showed the reaction to be complete. The NH$_4$OH was evaporated under reduced pressure and the residue was dissolved in 5-10 ml of hot distilled water and dried in a lyophillizer over the weekend. The yellow solids were then washed thoroughly with acetone and the residue was dried in a lyophillizer overnight to furnish 1.6 g of analog 16 as a yellow solid.

Example 5

Preparation of Branched methyl esters from the p-toluenesulfonyloxymethyl phosphonates Branched methyl esters were prepared from the p-toluenesulfonyloxymethylphosphonates 18 as illustrated in Scheme 4, using synthesis of (S)-HPMPA esters for purposes of illustration. The procedure is based on the method reported by Beadle et al., J. Med. Chem. 49:2010-2015, 2006.

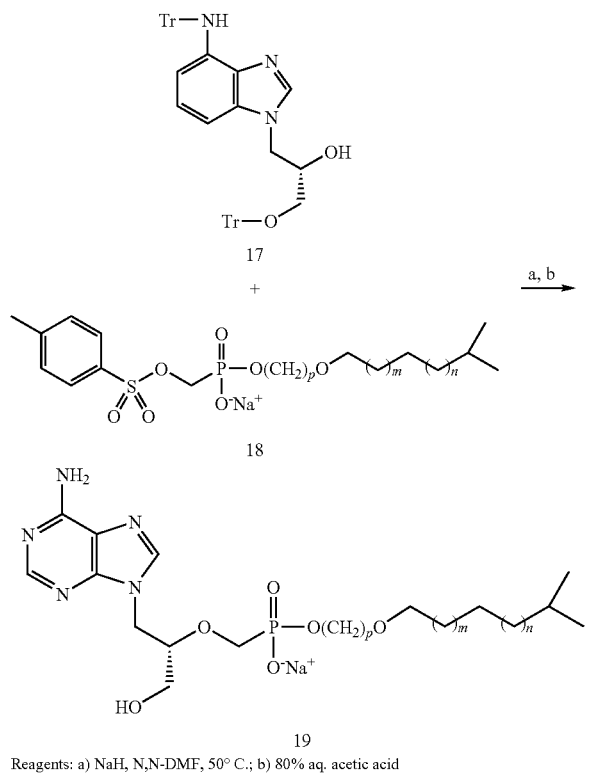

Reagents: a) NaH, N,N-DMF, 50° C.; b) 80% aq. acetic acid

General procedure for preparation of branched methyl alkoxyalkyl p-toluenesulfonyloxymethylphosphonates 18. Diethyl toluenesulfonyloxymethylphosphonate was synthesized from diethyl hydroxymethylphosphonate as described by Holý and Rosenberg, ((1982) Collect. Czech. Chem. Commun. 47:3447-3463). Bromotrimethylsilane (27 g, 175 mmol) was added to a solution of diethyl toluenesulfonyloxymethylphosphonate (9.5 g, 29.5 mmol) in dichloromethane (anhydrous, 150 mL). The mixture was stirred at room temperature under a $N_2$ atmosphere for 18 h. The mixture was then concentrated under vacuum to remove solvent and excess TMSBr, then redissolved in dichloromethane (150 mL) and cooled to 0° C. with an ice bath. N,N-DMF (0.5 mL) was added, and a solution of oxalyl chloride (22 g, 175 mmol) in $CH_2Cl_2$ (50 mL) was added dropwise over 30 min, and then the solution was stirred an additional 5 h. The mixture was evaporated to an oil, which was redissolved in $Et_2O$ (100 mL).

A solution of the branched methyl alkoxyalkanol 6 (21.5 mmol) and pyridine (10 mL) in $Et_2O$ (50 mL) was added, and stirring was continued for about 3 hours or until TLC analysis (1:1 hexanes/ethyl acetate) indicated complete phosphonylation of the alcohol. The reaction mixture was then added to cold saturated $NaHCO_3$ and vigorously stirred one hour. After hydrolysis was complete, the organic layer was separated, dried over $MgSO_4$ and evaporated under vacuum to give the crude esters, which were purified by flash chromatography (15% $EtOH/CH_2Cl_2$).

3-(15-methyl hexadecyloxy)propyl p-toluenesulfonyloxymethylphosphonate was prepared using this procedure, MS-ESI (m/z) 561.07 $(M+Na)^+$.

General procedure for preparation of branched methyl esters from the p-toluenesulfonyloxymethylphosphonates 18 is illustrated in Scheme 4 using (S)-HPMPA for purposes of illustration. Briefly, (S)-9-[3-trityloxy-2-hydroxypropyl]-N6-trityl-adenine 17 was prepared from adenine and (S)-trityl glycidyl ether (Daiso Co., Ltd., Japan) following the method of Webb ((1989) Nucleosides & Nucleotides 8:619-624). Sodium hydride (24 mg, 1.0 mmol) was added to a stirred solution of (S)-9-[3-trityloxy-2-hydroxypropyl]-$N^6$-trityladenine (640 mg, 0.62 mmol) in dry triethylamine (10 mL). After 15 min., the appropriate alkoxyalkyl toluenesulfonyloxymethylphosphonate (0.65 mmol) was added and the reaction mixture was heated to 50° C. and kept overnight. After cooling, the mixture was quenched with brine and extracted with ethyl acetate (3×15 mL). The organic extracts were dried over $MgSO_4$ and concentrated under vacuum to provide the fully protected (S)-HPMPA esters. The residue was purified by flash chromatography (10% $EtOH/CH_2Cl_2$). For purposes of illustration 3-(15-methyl-hexadecyloxy)propyl (S)-9-[3-trityloxy-2-(phosphonomethoxy)propyl]-$N^6$-trityl-adenine was prepared using this general method.

Deprotection and isolation of (S)-HPMPA alkoxyalkyl esters 19. Fully protected (S)-HPMPA esters were suspended in 80% aqueous acetic acid (20 mL/mmol) and heated to 60° C. for 1 hour, or until detritylation was complete as determined by TLC analysis. After cooling, the solvent was evaporated and the products 19 were purified by flash chromatography. Elution with 30% $MeOH/CH_2Cl_2$ provided 3-(15-methylhexadecyloxy)propyl (S)-HPMPA, MS-ESI (m/z) 600.32 $(MH)^+$ as a white solid.

Example 6

Preparation of alkenyloxyalkyl esters of acyclic nucleoside phosphonates

A general method for the synthesis of alkenyloxyalkyl esters having a terminal double bond is outlined in Scheme 5 using the nucleoside phosphonate cidofovir for purposes of illustration.

Scheme 5

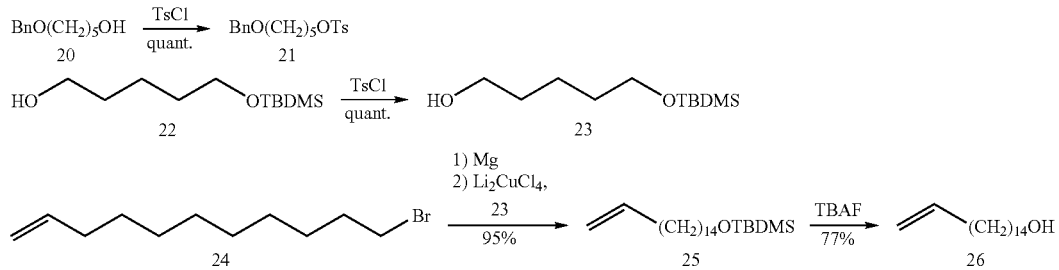

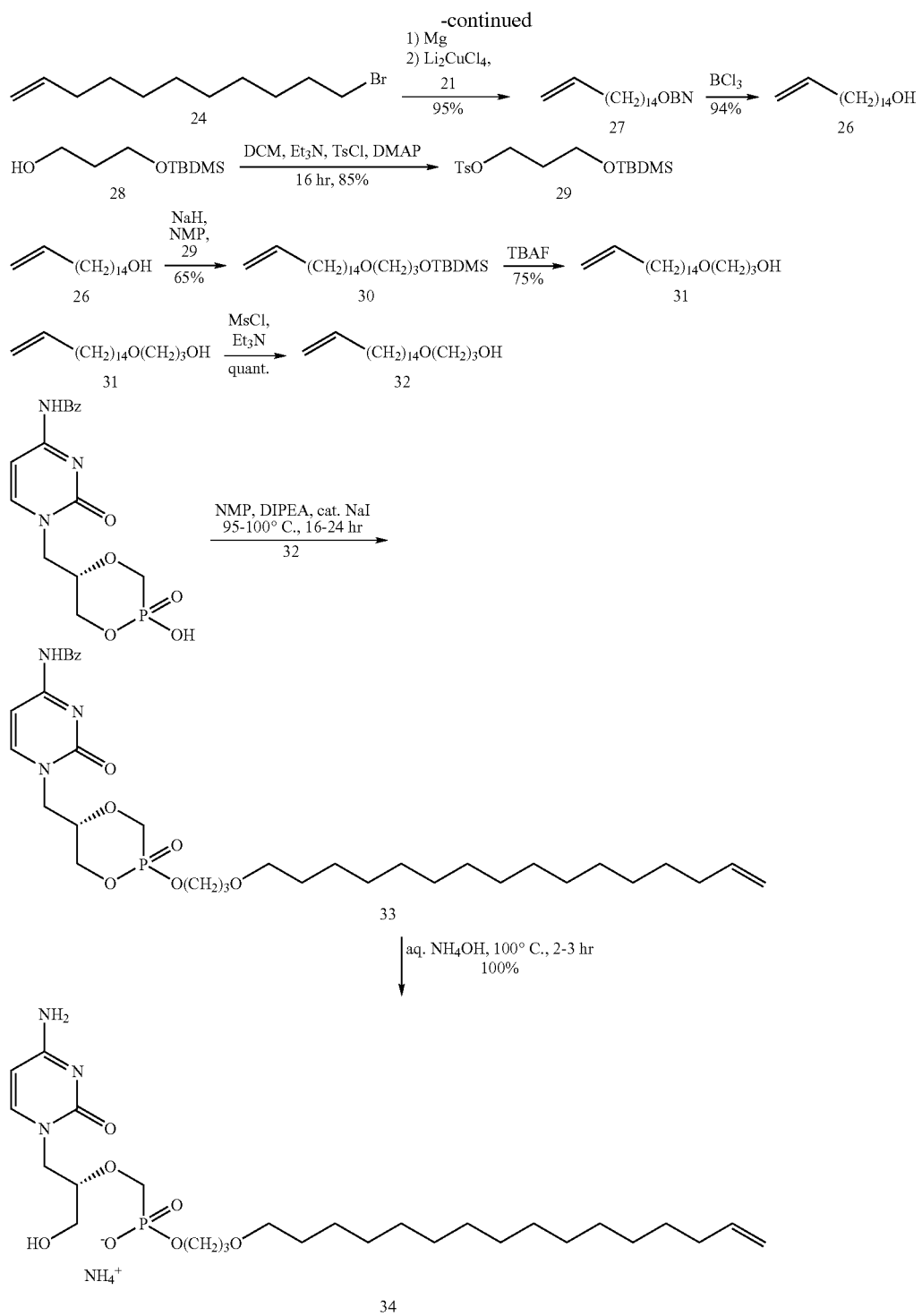

Toluene-4-sulfonic acid-5-benzyloxy-pentyl ester (21). 4.0 g (20 mmol) of commercially available 20 was dissolved in 40 mL of dry DCM. 4.2 mL (30 mmols) of Et$_3$N was added followed by 4.2 g (22 mmols) of TsCl and catalytic DMAP and the reaction was stirred for 16 h. 100 mL of DCM was then added and the reaction mixture was washed successively with saturated aq. NaHCO$_3$ (1×), water (1×) and brine (1×), dried over MgSO$_4$, and the solvent was evaporated under reduced pressure. The crude was purified by combiflash using hexane/ethyl acetate as an eluent to furnish 7.0 g of tosylate 21 in quantitative yield as colorless oil.

Toluene-4-sulfonic acid-5-tert-butyl-dimethyl-silanyloxy-pentyl ester (23). 5.0 mL (20 mmols) of commercially available 22 was dissolved in 40 mL of dry DCM. 4.2 mL (30 mmols) of Et$_3$N was added followed by 4.2 g (22 mmols) of TsCl and catalytic DMAP and the reaction was stirred for 16 h. 100 mL of DCM was then added and the reaction mixture was washed successively with saturated aq. NaHCO$_3$ (1×), water (1×) and brine (1×), dried over MgSO$_4$, and the solvent was evaporated under reduced pressure. The crude product was purified by combiflash using hexane/ethyl acetate as an eluent to furnish 7.4 g of target tosylate 23 in quantitative yield as colorless oil.

Tert-butyl-hexadec-15-enyloxy-dimethylsilane (25). Into a clean flame dried and Ar flushed 500 mL RBF was added 14.2 mL (65 mmol) of commercially available 24. To this was added 100 mL of anhydrous THF, 1.9 g (78 mmol) of Mg turnings and a pellet of I$_2$ to accelerate the reaction and the reaction mixture was refluxed for 2 h. It was then cooled to room temperature and further to −78° C. To this was added 7.4 g (20.0 mmol) of 23 in 20 mL of anhydrous THF followed by addition of 6.5 mL (0.65 mmol) of lithium cuprate. The resulting mixture was allowed to warm to room temperature while stirring overnight followed by quenching with saturated aq. NH$_4$Cl and extracted with EtOAc (3×). The combined EtOAc layer was then successively washed with water, saturated aq. NaHCO$_3$ and brine, dried over MgSO$_4$ and the solvents evaporated under reduced pressure. The residue was then purified by combiflash using hexane/EtOAc as eluent to furnish 6.7 g of 25 as colorless oil in 95% yield.

Hexadec-15-en-1-ol (26). To 11.0 g (31 mmol) of 25 was added 124 mL of a 1 M solution of TBAF in THF and the reaction was stirred for 16 h at room temperature. The reaction mixture was then quenched with saturated solution of aq. NH$_4$Cl and THF was evaporated under reduced pressure. The aq. solution was then diluted with 200 mL of water and the target product was extracted with Et$_2$O (3×), the combined organic layers were then washed with brine (1×), dried over MgSO$_4$ and the solvent was removed under reduced pressure. The crude was then purified by combiflash using hexane/ethyl acetate as eluent to furnish 5.7 g of target product 26 in 77% yield as colorless oil.

Hexadec-15-enyloxymethyl-benzene (27). Into a clean flame dried and Ar flushed 500 mL RBF was added 14.2 mL (65 mmol) of commercially available 24. To this mixture was added 100 mL of anhydrous THF, 1.9 g (78 mmol) of Mg turnings and a pellet of I$_2$ to accelerate the reaction. The reaction mixture was refluxed for 2 h and then cooled to room temperature and further to −78° C. To this was added 7.0 g (20.0 mmol) of 21 in 20 mL of anhydrous THF followed by addition of 6.5 mL (0.65 mmol) of lithium cuprate. The resulting mixture was allowed to warm to room temperature while stirring overnight followed by quenching with saturated aq. NH$_4$Cl and extracted with EtOAc (3×). The combined EtOAc layers were then successively washed with water, saturated aq. NaHCO$_3$ and brine, dried over MgSO$_4$ and the solvents evaporated under reduced pressure. The residue was then purified by combiflash using hexane/EtOAc as eluent to furnish 6.3 g of the compound 27 as colorless oil in 95% yield.

Hexadec-15-en-1-ol (26). Into clean flame dried Ar flushed 500 mL RBF was placed 6.3 g (19 mmol) of 27 and 100 mL of dry DCM and the mixture was cooled to −78° C. 95 mL of BCl$_3$ (1.0 M solution in DCM) was then slowly added to the above solution. After complete addition the cooling bath was removed and the reaction mixture was allowed to warm to room temperature. Stirring was continued for an additional 30 minutes at room temperature after which the reaction was cooled in an ice-water bath and quenched very cautiously!! (as it turns violent) with 100 mL of water. The organic layer was then separated and washed with water, dried over MgSO$_4$ and the solvents evaporated under vacuum. The crude was then purified with combiflash using hexane/ethylacetate as eluent to furnish 4.3 g of 26 in 94% yield.

Toluene-4-sulfonic acid-3-tert-butyl-dimethyl-silanyloxypropyl ester (29). 25.0 mL (115 mmols) of commercially available 28 was dissolved in 100 mL of dry DCM and 24.2 mL (173 mmols) of Et$_3$N was added and the mixture was cooled to 0° C. To this solution was then added 24.2 g (127 mmols) of TsCl and catalytic DMAP. The reaction was stirred for 16 h. 300 mL of DCM was then added and the reaction mixture was washed successively with saturated aq. NaHCO$_3$ (1×), water (1×) and brine (1×), dried over MgSO$_4$, and the solvent was evaporated under reduced pressure. The crude was purified by combiflash using hexane/ethyl acetate as an eluent to furnish 34 g of target tosylate 29 in 85% yield as colorless oil.

Tert-butyl-3-hexadec-15-enyloxy-propoxy-dimethylsilane (30). Into a clean flame dried and Ar flushed 2 L RBF was added 12 g (50 mmol) of (26) and 150 mL of anhydrous DMF was added. This solution was then cooled to 0° C. and 2.6 g (65 mmol) of NaH was added slowly. After complete addition the reaction was stirred at room temperature for 30 minutes and cooled to 0° C. 34.5 g (100 mmol) of 29 was then slowly added to the reaction with vigorous stirring. After complete addition the reaction mixture was heated at 80° C. for 2 h at which time TLC showed complete consumption of 26. The reaction was then cooled to room temperature and quenched with dropwise addition of saturated aq. NH$_4$Cl. 200 mL of water was added and the target product was extracted with EtOAc (3×), the combined organic layers were successively washed with water (3×), brine (1×) and dried over MgSO$_4$. The solvent was evaporated under reduced pressure and the residue was purified by combiflash using hexane/ethyl acetate as an eluent to furnish 13.3 g of 30 as yellow oil in 65% yield.

3-Hexadec-15-enyloxy-propanol (31). To 13.1 g (31.8 mmol) of 30 was added 128 mL of a 1 M solution of TBAF in THF and the reaction was stirred for 16 h at room temperature. The reaction mixture was then quenched with saturated solution of aq. NH$_4$Cl and THF was evaporated under reduced pressure. The aq. solution was then diluted with 200 mL of water and the product was extracted with Et$_2$O (3×), the combined organic layers were then washed with brine (1×), dried over MgSO$_4$ and the solvent was removed under reduced pressure. The crude was then purified by combiflash using hexane/ethyl acetate as eluent to furnish 7.1 g of target product 31 in 75% yield as colorless oil.

Methanesulfonic acid-3-hex-dec-15-enyloxy-propyl ester (32). To 7.1 g (23.7 mmol) of 31 was added 20 mL of DCM and 5.0 mL (36 mmol) of Et$_3$N and the solution was cooled to 0° C. To this cooled solution was added dropwise 2.0 mL (26 mmol) of MsCl and a catalytic amount of DMAP. The reaction was stirred at room temperature overnight. The reaction mixture was then diluted with 50 mL of DCM and washed successively with saturated solution of aq. NaHCO$_3$ (1×), water (1×) and brine (1×), dried over MgSO$_4$ and the solvent was evaporated under reduced pressure. The crude product was then purified by combiflash using hexane/ethyl acetate as eluent to furnish 9 g of target product 32 in quantitative yield.

Substitution of (32) with Bz-c-CDV. 1.7 g (4.6 mmol) of Bz-c-CDV was dissolved in 10 mL of NMP and 1.2 mL (7 mmol) of DIPEA was added to it followed by 9 g (23.9 mmol) of 32. The reaction was heated at 95-100° C. for 24 h at which time the TLC showed the product together with some Bz-c-CDV. At this stage the reaction was allowed to proceed for an additional 4 h, but as the TLC did not show much progress, the reaction mixture was cooled to room temperature and the solvent was evaporated under high vacuum. The residue was purified by combiflash using chloroform/MeOH as eluent to furnish 1.33 g of target product 26 as yellow oil in 45% yield.

Deprotection and hydrolysis of (33). To 1.3 g (2.0 mmol) of 33 was added 30 mL of concentrated NH$_4$OH and the sealed tube was heated at 95° C. for 2-3 h at which time the solution turns clear. The reaction mixture was then cooled and the TLC showed the reaction to be complete. The NH$_4$OH was evaporated under reduced pressure and the residue was dissolved in 5-10 mL of hot water and dried in lyophilizer over the weekend. The yellow solids were then washed thoroughly with acetone and the residue was dried in lyophilizer for overnight to furnish 1.1 g of analog 34 as a yellow solid.

Example 7

Preparation of penultimate fluorinated alkoxyalkyl esters of acyclic nucleoside phosphonates A general procedure for the preparation of penultimate fluorinated alkoxyalkyl esters of acyclic nucleoside phosphonates is illustrated in Scheme 6, below. Fluoroalkoxyalkyl esters of acyclic nucleoside phosphonates such as 3-(15-fluoro-hexadecyloxy)propyl cidofovir 42 (15-F-HDP-CDV) and 3-(15-fluoro-hexadecyloxy)propyl (S)-HPMPA 43 (15-F-HDP-(S)-HPMPA) can be prepared using this process. Briefly, with reference to Scheme 6, commercially available 2-bromopropanoic acid 35 is reduced to the alcohol with borane:THF complex solution to provide 2-bromo-1-propanol 36. Fluorination of 36 is achieved with 1,1,2-trifluoro-2-chloroethyldiethylamine, a mild and safe reagent to convert 1-hydroxy-2-halogenoalkanes into the corresponding rearranged fluoride 37. Conversion of 37 into a Grignard reagent followed by reaction with 13-bromo-tridecanol in the presence of the catalyst provides 15-fluorohexadecanol 38. Conversion of alcohol 38 into the methanesulfonate derivative, followed by reaction with 1,3-propanediol provides 3-(15-fluorohexadecyloxy)propan-1-ol 39. Reaction of 39 with cyclic cidofovir or cyclic (S)-HPMPA as described generally in Example 2 (step a), provides the cyclic esters (40 and 41, respectively) which can then be converted to the desired compounds (42 and 43, respectively) using the general method set forth in Example 2 (step b).

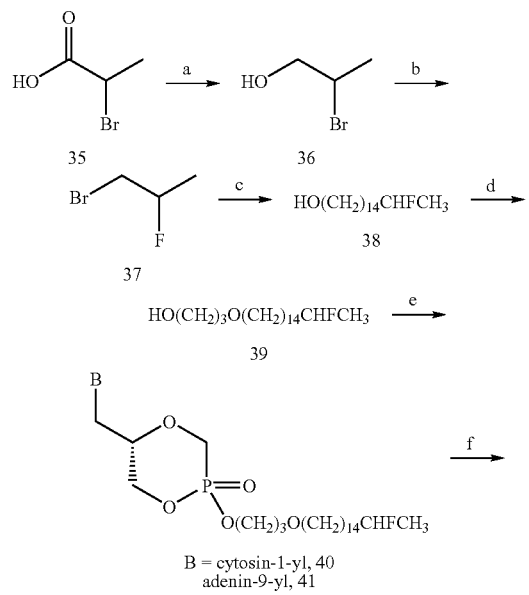

Scheme 6

B = cytosin-1-yl, 40
adenin-9-yl, 41

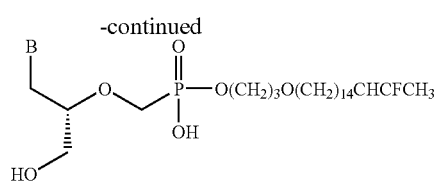

3-(15-fluorohexadecyloxy)propyl CDV, 42
3-(15-fluorohexadecyloxy)propyl (S)-HPMPA, 43

Reagents: a) BH$_3$, THF; b) fluoroamine; c) Mg/13-bromo-tridecanol, Li$_2$CuCl$_4$; d) methanesulfonyl chloride, pyridine, then 1,3-propanediol, NaH, N,N-DMF; e) cCDV or cHPMPA, DIAD, PPh$_3$, N,N-DMF; f) 1M NaOH Example 8

Preparation of Terminal fluorinated alkoxyalkyl esters of acyclic nucleoside phosphonates A general procedure for the preparation of terminal fluorinated alkoxyalkyl esters of acyclic nucleoside phosphonates is illustrated in Scheme 7, below. Fluoroalkoxyalkyl esters of acyclic nucleoside phosphonates such as 3-(16-fluoro-hexadecyloxy)propyl cidofovir (16-F-HDP-CDV) 49 and 3-(16-fluoro-hexadecyloxy)propyl (S)-HPMPA 50 (16-F-HDP-(S)-HPMPA) can be prepared using this process. Briefly, with reference to Scheme 7, the Grignard reagent prepared from 1-bromo-4-fluorobutane and magnesium is reacted with 12-bromododecanol 44 to obtain 16-fluorohexadecanol 45. Reaction of 45 with methanesulfonyl chloride followed by reaction with 1,3-propanediol provides 16-fluorohexadecyloxy-1-propanol 46. Coupling of 46 with cyclic cidofovir or cyclic (S)-HPMPA as described generally in Example 2 (step a), provides the cyclic esters (47 and 48, respectively) which can then be converted to the desired compounds (49 and 50, respectively) using the general method set forth in Example 2 (step b).

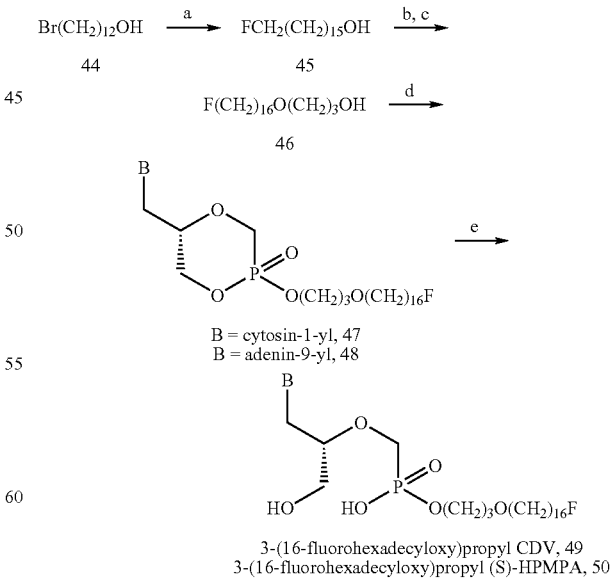

Scheme 7

B = cytosin-1-yl, 47
B = adenin-9-yl, 48

3-(16-fluorohexadecyloxy)propyl CDV, 49
3-(16-fluorohexadecyloxy)propyl (S)-HPMPA, 50

Reagents: a) Mg/1-bromo-4-fluorobutane, Li$_2$CuCl$_4$, THF; b) methanesulfonyl chloride, pyridine; c) 1,3-propanediol, NaH, N,N-DMF; d) cCDV or cHPMPA, DIAD, PPh$_3$, N,N-DMF; e) 1M NaOH

Example 9

Preparation of Terminal pentafluorinated alkoxyalkyl esters of acyclic nucleoside phosphonates A general procedure for the preparation of terminal pentafluorinated alkoxyalkyl esters of acyclic nucleoside phosphonates is illustrated in Scheme 8.

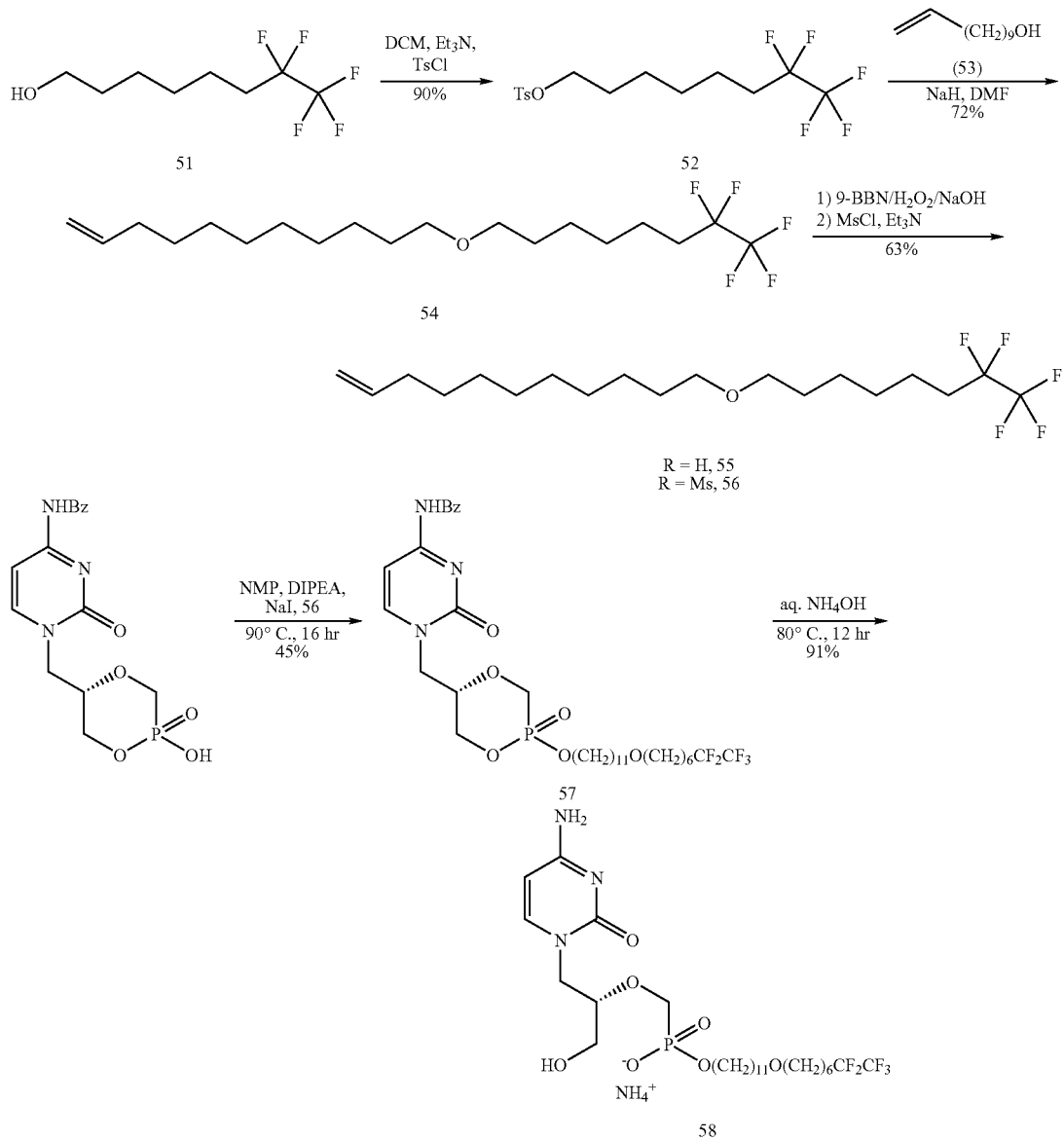

Toluene-4-sulfonic acid 7,7,8,8,8-pentafluoro octyl ester (52). Into a clean flame dried 250 mL RBF under current of $N_2$, was added 11.8 g (53.6 mmol) of commercially available 51 which was then dissolved in 100 mL of dry DCM. To this was added 11.2 mL (80.4 mmol) of triethylamine and the flask was cooled in an ice bath. To this was slowly added 11.3 g (59 mmol) of TsCl followed by 62 mg (0.50 mmol) of DMAP. The reaction mixture was stirred for 3 h after which it was diluted with 100 mL of DCM and successively washed with saturated solution of $NaHCO_3$, $H_2O$ and brine, dried over $MgSO_4$, filtered and evaporated to dryness. The residue was purified using combiflash (120 g silica column) with hexane/ethyl acetate as solvents to furnish 18 g (90%) of the target product 52 as colorless oil.

11-(7,7,8,8,8-pentafluoro-octyloxy)-undec-1-ene (54). Into a clean flame dried 1 L RBF under current of $N_2$, was added 100 mL of dry DMF and 20 mL (96 mmols) of commercially available 53. 2.3 g (57.6 mmol) of NaH was added to the reaction and the mixture was stirred for 3 h at room temperature. 18 g (48 mmols) of 52 was dissolved in 50 mL of DMF and was slowly added to the above reaction mixture. After complete addition the stirring was continued for 2 h at room temperature and at 80° C. for 2 h. The reaction was then cooled in an ice bath and quenched with a solution of saturated aq. $NH_4Cl$. 300 mL of water was then added and reaction mixture was extracted with DCM (4×). The combined DCM layers were then washed with $H_2O$ (3×), brine (1×), dried over $MgSO_4$, filtered and the solvent was evaporated under vacuum. The residue was then purified using combiflash (120 g silica column) with hexane/ethyl acetate as eluent to furnish 12.86 g (72%) of the target product 54 as colorless oil.

11-(7,7,8,8,8-pentafluoro-octyloxy)-undecan-1-ol (55). Into a clean flame dried 1 L RBF under current of $N_2$, was put 12.86 g (34.48 mmol) of 54. To this was added 172 mL (86.2 mmol) of 9-BBN (0.5 M in THF). The reaction was stirred for 3 h. 23 mL of 30% $H_2O_2$ was then added dropwise to the reaction mixture followed by 49 mL of 15% aq. NaOH and the reaction mixture was stirred at 85° C. for 3 h. The mixture was then cooled to room temperature and THF was evaporated and the residue was diluted with $H_2O$ and extracted with EtOAc (3×). The combined organic layer was then washed with brine (1×), dried over $MgSO_4$, filtered and the solvent was evaporated under vacuum. The residue was then purified using combiflash (120 g silica column) with hexane/ethyl acetate as eluent to furnish 10.15 g (76%) of compound 55 as a white solid.

Methanesulfonic acid 11-(7,7,8,8,8-pentafluoro-octyloxy)-undecyl ester (56). Into a clean flame dried 250 mL RBF under current of $N_2$, was added 10.10 g (26 mmol) of 55. To this was added 100 mL of DCM and 5.5 mL (39 mmol) of $Et_3N$. The reaction mixture was then cooled in an ice-water bath and 2.3 mL (29 mmol) of MsCl was added and stirred for 12 h at room temperature. The reaction was then diluted with 200 mL of DCM and washed successively with sat. aq. $NaHCO_3$ (1×), $H_2O$ (2×), brine (1×), dried over $MgSO_4$, filtered and the solvent evaporated under vacuum. The residue was then purified using combiflash (120 g silica column) with hexane/ethyl acetate as eluent to furnish 10.15 g (84%) of target product 56 as a white solid.

11-(7,7,8,8,8-pentafluoro-octyloxy)-undecyl $N^4$-benzoyl-cyclic cidofovir (57). Into a clean flame dried 250 mL RBF under current of $N_2$, was placed 2.0 g (5.45 mmol) of benzoyl protected c-CDV followed by 40 mL of dry NMP and the mixture was stirred until the solution turned clear. To this was then added 2.9 mL (16.35 mmol) of DIPEA and 10.15 g (21.7 mmols) of 56 followed by 1.3 g (11 mmol) of NaI. The reaction mixture was then stirred at 90° C. for 16 h. Solvents were then evaporated under vacuum and the residue was purified using combiflash (120 g silica column) with $CHCl_3$/MeOH as eluent to furnish 1.8 g (45%) of the target product 57 as a yellow solid.

11-(7,7,8,8,8-pentafluoro-octyloxy)-undecyl cidofovir, ammonium salt (58). 1.8 g (2.44 mmol) of 57 was put in a tube and 40 mL of $NH_4OH$ was added and the tube was sealed. The reaction mixture was then stirred at 80° C. in the sealed tube for 12 h. It was then cooled to room temperature after which $NH_4OH$ was evaporated under vacuum and the residue was dissolved in 10 mL of $H_2O$ and lyophilized. The whitish yellow solid was then washed with acetone (6×) and filtered under suction. The solids were then dried in high vacuum for 16 h to furnish 1.46 g (91%) of the target product 58 as whitish yellow solid in the form of ammonium salt. $^1H$ NMR, $^{31}P$ NMR, $^{19}F$ NMR, elemental analysis and LRMS data were all consistent with the structure of the target product 58.

Example 10

Evaluation of Antiviral Activity of penultimate Branched methyl alkoxyalkyl Analogs of cidofovir (CDV) and 9-(S)-(3-hydroxy-2-phonomethoxypropyl)-adenine ((S)-HPMPA) Against Vaccinia Virus and Cowpox Virus in Vitro Virus pool preparation. The vaccinia virus strain, Copenhagen, and cowpox virus, strain Brighton, stock pools were obtained from John Huggins of the U.S. Army Medical Research Institute for Infectious Diseases, Frederick, Md. These pools were prepared in Vero cells and were diluted 1:50 to provide working stocks.

Plaque reduction assay for efficacy. Two days prior to use, HFF cells were plated on six-well plates and incubated at 37° C. with 10% $CO_2$ and 90% humidity. On the day of the assay, the drugs were made up at twice the desired concentration in 2× minimal essential medium (MEM) containing 5% fetal bovine serum (FBS) and antibiotics and diluted serially 1:5 in 2×MEM to provide six concentrations of drug. The initial starting concentration was usually 200 μM and ranged down to 0.06 μM. The virus to be used was diluted in MEM containing 10% FBS to a desired concentration which would give 20 to 30 plaques per well. The medium was then aspirated from the wells, and 0.2 mL of virus was added to each well in triplicate, with 0.2 mL of medium being added to drug toxicity wells. The plates were incubated for 1 h with shaking every 15 min. After the incubation period, an equal amount of 1% agarose was added to an equal volume of each drug dilution. This gave final drug concentrations beginning with 100 μM and ending with 0.03 μM and a final agarose overlay concentration of 0.5%. The drug-agarose mixture was added to each well in 2 mL volumes, and the plates were incubated for 3 days, after which the cells were stained with a 1.5% solution of neutral red. After a 5- to 6-h incubation period, the stain was aspirated and the plaques were counted using a stereomicroscope at ×10 magnification. The MacSynergy II, version 1, computer program was used to calculate the 50% effective concentration ($EC_{50}$). The results are set forth in Tables 3 and 4.

Neutral-red uptake assay for toxicity. Twenty-four hours prior to the assay, HFF cells were plated on 96-well plates at a concentration of 2.5×10⁵ per mL. After 24 h, the medium was aspirated and 125 μL of drug was added to the first row of wells and then diluted serially 1:5 using the Beckman BioMek liquid-handling system. After the addition of the drug, the plates were incubated for 7 days in a $CO_2$ incubator at 37° C. At that time, the medium with drug was aspirated, and 200 μl of 0.01% neutral red in phosphate-buffered saline (PBS)/well was added and incubated for 1 h. The dye was aspirated, and the cells were washed with PBS using a Nunc plate washer. After the PBS was removed, 200 μL of 50% ethanol-1% glacial acetic acid (in $H_2O$)/well was added. The plates were placed on a rotary shaker for 15 min, and the optical densities were read at 540 nm on a Bio-tek plate reader. The results are set forth in Tables 3 and 4.

TABLE 3

Activity of penultimate branched methyl alkoxyalkyl analogs of CDV against vaccinia virus and cowpox virus in HFF cells

| Compound | $CC_{50}$ (μM) | Vaccinia Copenhagen $EC_{50}$ (μM) | $SI^a$ | Cowpox Brighton $EC_{50}$ (μM) | $SI^a$ |
|---|---|---|---|---|---|
| CDV | >317 ± 0 | 19 ± 9.9 | >17 | 31 ± 1.7 | >10 |
| HDP-CDV | 94 | 0.2 | 470 | 0.2 | 470 |
| 15M-HDP-CDV | 15.2 ± 5.5 | 0.10 | 152 | 0.34 | 45 |
| 14M-PDP-CDV | 18 ± 1.1 | 0.14 | 129 | 0.13 | 139 |

TABLE 3-continued

Activity of penultimate branched methyl alkoxyalkyl analogs of CDV against vaccinia virus and cowpox virus in HFF cells

| Compound | $CC_{50}$ (μM) | Vaccinia Copenhagen | | Cowpox Brighton | |
|---|---|---|---|---|---|
| | | $EC_{50}$ (μM) | SI[a] | $EC_{50}$ (μM) | SI[a] |
| 13M-TDP-CDV | 41 ± 2 | 0.13 | 315 | 0.20 | 205 |
| 12M-TrDP-CDV | 44 ± 5.4 | 0.70 | 63 | 0.90 | 49 |
| 17M-ODE-CDV | 15 ± 4 | 0.032 | 469 | 0.05 | 300 |

[a]SI (Selectivity Index) = $CC_{50}/EC_{50}$
Abbreviations: CDV, cidofovir; HDP-CDV, hexadecyloxypropyl-CDV; 17M-ODE-CDV, 17-methyl-octadecyloxyethyl cidofovir; 15M-HDP-CDV, 15-methyl-hexadecyloxypropyl cidofovir; 14M-PDP-CDV, 14-methyl-pentadecyloxypropyl cidofovir; 13M-TDP-CDV, 13-methyl-tetradecyloxypropyl cidofovir; 12M-TrDP-CDV, 12-methyl-tridecyloxypropyl cidofovir

TABLE 4

Activity of penultimate branched methyl alkoxyalkyl analogs of (S)-HPMPA against vaccinia virus and cowpox virus in HFF cells

| Compound | $CC_{50}$ (μM) | Vaccinia Copenhagen | | Cowpox Brighton | |
|---|---|---|---|---|---|
| | | $EC_{50}$ (μM) | SI[a] | $EC_{50}$ (μM) | SI[a] |
| CDV | >317 | 19.4 | >16 | 38.1 | >8.3 |
| HDP-(S)-HPMPA | 31.8 | 0.010 | 3,180 | 0.018 | 1767 |
| 15M-HDP-(S)-HPMPA | 27.5 | 0.012 | 2,292 | 0.052 | 529 |
| ODE-(S)-HPMPA | 2.1 | 0.008 | 263 | 0.012 | 175 |
| 17M-ODE-(S)-HPMPA | 0.8 | 0.009 | 89 | 0.011 | 73 |

[a]SI (Selectivity Index) = $CC_{50}/EC_{50}$
Abbreviations: CDV, cidofovir; (S)-HPMPA, 9-(S)-(3-hydroxy-2-phosphonomethoxypropyl)-adenine; HDP-, hexadecyloxypropyl; ODE-, octadecyloxypropyl; 15M-HDP-, 15-methyl-hexadecyloxypropyl-; 17M-ODE-, 17-methyl-octadecyloxyethyl- Example 11

Evaluation of Antiviral Activity of penultimate Branched methyl alkoxyalkyl Analogs of CDV and (S)-HPMPA Against Ectromelia Virus in Vitro Cells and Viruses. BS-C-1 cells (ATCC CCL 26) were grown in Dulbecco's modified Eagle's medium (DMEM) containing 10% bovine serum fetal clone III (Hyclone, Logan, Utah), 2 mM L-glutamine (GIBCO, Grand Island, N.Y.), 100 U/mL penicillin (GIBCO), and 100 μg/mL streptomycin (GIBCO). A plaque-purified isolate of the MOS strain of ECTV (ATCC VR-1374) designated MOS-3-P2 was propagated in an African green monkey kidney cell line, BS-C-1. Virus was purified through a sucrose cushion. Virus suspensions were serially diluted in PBS+1% sera, absorbed to monolayers for 1 h at 37° C., and overlayed with a suspension of 1% carboxyl methyl cellulose in DMEM+5% Fetal clone III. After 4 days at 37° C., virus plaques were visualized and virus inactivated by the addition to each well of 0.5 mL of a 0.3% crystal violet/10% formalin solution.

Plaque reduction assay. CV-1 cells were plated in wells of a 24-well cluster plate. Each monolayer was infected with 75 plaque forming units (PFU) of indicator virus in 0.1 mL of DMEM+5% Fetal clone III for 60 min at 37° C. Media was removed by aspiration and standard virus overlay media containing no drug or the test drug at concentrations ranging from 0.05 to 50 μM was added. The plates were incubated at 37° C. for 3-4 days for ECTV and 2 days for VACV-WR, monolayers were stained, and plaques counted using a stereomicroscope. The $EC_{50}$ concentration for each drug was calculated. The results are set forth in Table 5.

TABLE 5

Activity of penultimate branched methyl alkoxyalkyl analogs of CDV and (S)-HPMPA against ectromelia infection in vitro

| | Ectromelia Virus | | |
|---|---|---|---|
| Compound | $CC_{50}$ (μM) | $EC_{50}$ (μM) | SI |
| 12M-TrDP-CDV | 82 | 0.94 | 57 |
| 13M-TDP-CDV | 82 | 0.40 | 161 |
| 14M-PDP-CDV | 38 | 0.17 | 137 |
| HDP-CDV | 10 | 0.14 | 42 |
| 15M-HDP-CDV | 18 | 0.04 | 391 |
| 17M-ODE-CDV | 7.5 | 0.08 | 54 |
| HDE-HPMPA | 2.5 | 0.05 | 50 |
| 15M-HDE-HPMPA | 43 | 0.012 | 3.588 |

Abbreviations as set forth in Tables 3 and 4

Example 12

Activity of Oral 15M-HDP-(S)-HPMPA in Lethal Ectromelia Virus Infection

In vivo drug evaluation: A/Ncr mice were injected to effect with an anesthetic cocktail (ketamine 90 mg/kg/xylazine 10 mg/kg), held at 45° C. from the vertical on a intubation platform, and inoculated with 5 μl of virus suspension in each naris for a total challenge dose of 140 PFU (~280×LD50). Approximately 2.5 min following inoculation of virus, the mice were returned to their cage. Four hours following exposure to ECTV, groups of mice were treated by gavage with 0.1 ml of sterile, distilled water alone or water containing the test compound. This treatment was repeated on days 1, 2, 3, and 4 for a total of five doses. The mice were observed over 21 days for clinical signs of disease (morbidity) and mortality. The results are set forth in Table 6.

TABLE 6

Activity of oral HDP-(S)-HPMPA, HDP-CDV and penultimate branched methyl analogs against lethal ectromelia infection in vivo

| Treatment | Daily Dose, mg/kg | Mortality | MDD |
|---|---|---|---|
| Vehicle control | — | 5/5 | 7.6 |
| HDP-(S)-HPMPA | 2.5 | 5/5 | 9.4 |
| HDP-(S)-HPMPA | 5.0 | 1/5 | 11 |
| HDP-(S)-HPMPA | 10.0 | 0/5 | — |
| 15M-HDP-(S)-HPMPA | 2.5 | 3/5 | 14.3 |
| 15M-HDP-(S)-HPMPA | 5.0 | 0/5 | — |
| 15M-HDP-(S)-HPMPA | 10.0 | 0/5 | — |
| HDP-CDV | 2.5 | 2/5 | 13 |
| HDP-CDV | 5.0 | 0/5 | — |
| HDP-CDV | 10.0 | 0/5 | — |
| 13M-TDP-CDV | 2.5 | 4/5 | 9.3 |

TABLE 6-continued

Activity of oral HDP-(S)-HPMPA, HDP-CDV and penultimate branched methyl analogs against lethal ectromelia infection in vivo

| Treatment | Daily Dose, mg/kg | Mortality | MDD |
|---|---|---|---|
| 13M-TDP-CDV | 5.0 | 0/5 | — |
| 13M-TDP-CDV | 10.0 | 0/5 | — |
| 14M-PDP-CDV | 2.5 | 1/5 | 14 |
| 14M-PDP-CDV | 5.0 | 0/5 | — |
| 14M-PDP-CDV | 10.0 | 0/5 | — |

Abbreviations: HDP, hexadexyloxypropyl; 15M-HDP, 15-methyl-hexadecyloxypropyl; 13M-TDP, 13-methyl-tetradecyloxypropyl; 14M-PDP, 14-methyl-pentadecyloxypropyl. Drug administered orally 4 hrs after infection daily for 5 days. MDD, Mean day of death

Example 13

Metabolic Stability Testing with Liver S9 Fractions

Target compounds were incubated in pooled S9 liver fractions from monkey and human liver (purchased from a commercial source) at 37° C. The control sample (immediately quenched) was used to determine the response at time zero. The ratio between the response of the incubated samples and time zero indicated the % parent compound remaining. Compounds were dissolved in DMSO and serially diluted with buffer to a concentration suitable for the assay (1 to 10 µM). A portion of a high concentration dilution (~500 mM) was used to determine the LC-MS/MS conditions for analysis (ionization polarity, SRM transition, collision energy). 7-ethoxycoumarin was included as a control. Negative controls (without S9) were included to check the stability of the test compounds at incubation conditions. All assays were performed in triplicate and the % parent compound remaining was reported. Incubations were generally performed in microtiter plates with a protein concentration of 3 mg/mL and a compound concentration of 1 µM. Reactions were sampled at the specified time points and stopped by the addition of a cold acetonitrile/water solution. The quenched plates were centrifuged and subsequently analyzed by fast gradient LC-MS/MS. The results are set forth in FIG. 3.

The invention claimed is:
1. A nucleoside phosphate selected from the group of compounds having the following structures:

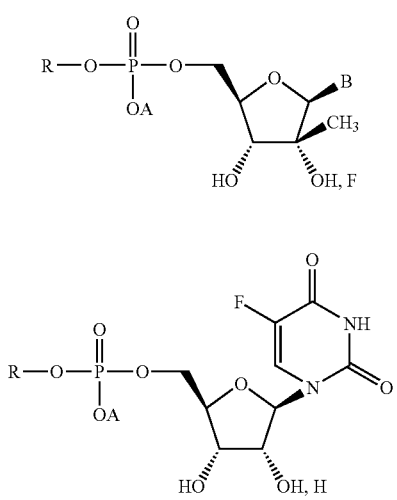

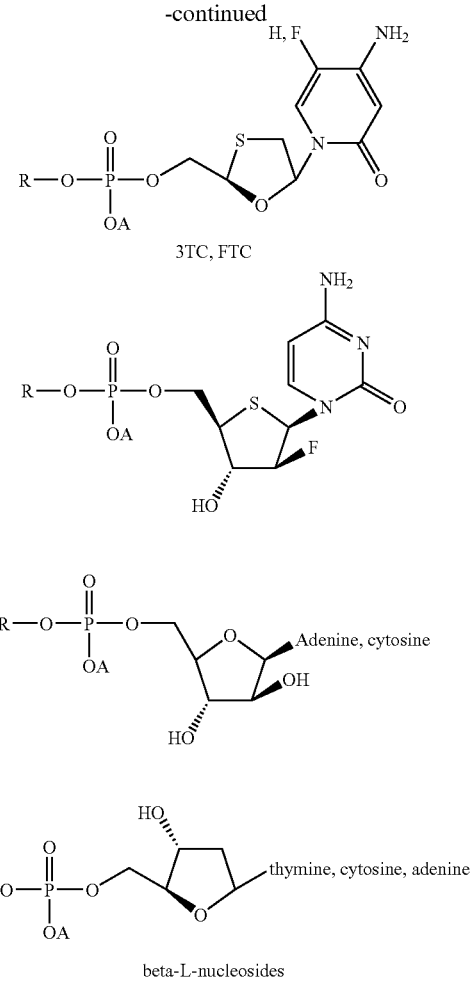

beta-L-nucleosides wherein
R is selected from the group consisting of —$R_1$—O—$R_2$, wherein $R_1$ is selected from the group consisting of an optionally substituted $C_1$ to $C_{11}$ alkyl group and $R_2$ is selected from the group consisting of a $C_6$ to $C_{17}$ alkyl group or a $C_6$ to $C_{17}$ alkenyl group;

wherein
said $C_6$ to $C_{17}$ alkyl group is substituted with one or more alkyl groups selected from the group consisting of methyl, ethyl, propyl, or cycloalkyl, including cyclopropyl and/or one or more halogens selected from the group consisting of F, Cl, Br and I; and further wherein said $C_6$ to $C_{17}$ alkyl group includes one or more substituents at or near the terminal position of the alkyl group; and wherein
said $C_6$ to $C_{17}$ alkenyl group is optionally-substituted with an alkyl group selected from the group consisting of methyl, ethyl, propyl, a cycloalkyl group including, cyclopropyl and/or one or more halogens selected from the group consisting of F, Cl, Br and I; and further wherein the said $C_6$ to $C_{17}$ alkenyl group contains one or more double bonds, including a terminal double bond;

B is selected from a purine or pyrimidine base; and

A is a counterion selected from the group consisting of $H^+$, $Li^+$, $Na^+$, $K^+$, $NH_4^+$, tetraalkyl ammonium and other tertiary amine salts including triethylamine.

2. The phosphate of claim 1 wherein R is selected from the group of compounds having the following structure:

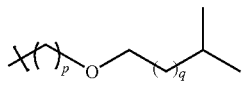

wherein p is selected from 1 to 11 and q is selected from 6 to 17.

3. The phosphate of claim 1 wherein R is selected from the group of compounds having the following structure:

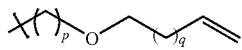

wherein p is selected from 1 to 11 and q is selected from 6 to 17.

6. The phosphate of claim 1 wherein R is selected from the group of compounds having the following structure:

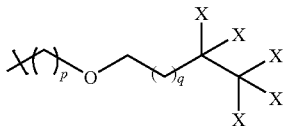

wherein p is selected from 1 to 11 and q is selected from 6 to 17 and X is independently selected from a halogen.

7. The phosphate of claim 6 wherein X is F.

8. The phosphate of claim 1 wherein R is selected from the group of compounds having the following structures:

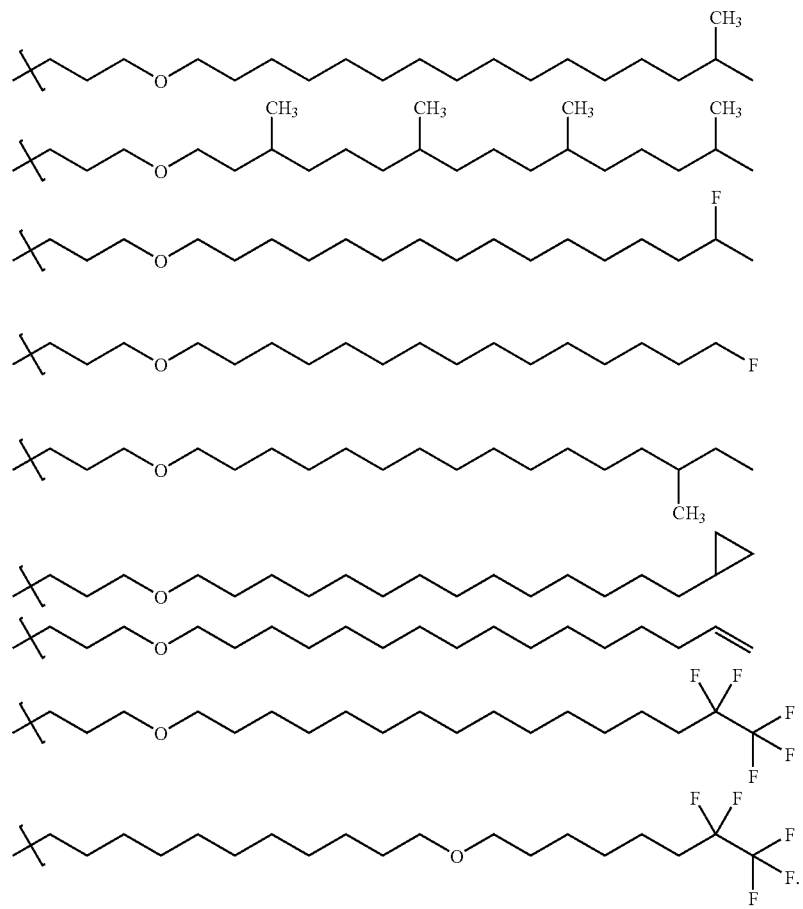

4. The phosphate of claim 1 wherein R is selected from the group of compounds having the following structure:

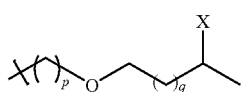

wherein p is selected from 1 to 11 and q is selected from 6 to 17 and X is a halogen.

5. The phosphate of claim 4 wherein X is F.

9. The nucleoside phosphate of claim 1 wherein R is selected to prevent or decrease metabolic degradation of the phosphonate.

10. The nucleoside phosphate of claim 1 wherein said phosphate is selected from an antiviral or an antineoplastic agent.

11. The nucleoside phosphate of claim 10, wherein said antiviral agent is a derivative of a compound selected from the group consisting of acyclovir, ganciclovir, AZT, ddI, ddA, d4T, ddC, 3TC, FTC, 2'-C-methyl adenosine, 2'-C-methyl guanosine, 7-deaza-2'-methyl adenosine, 2'-C-methyl cytosine, DAPD, L-FMAU, entecavir, telbivudine and various β-L-2'-deoxycytidine, β-L-2'-deoxyadenine and β-L-2'-deoxythymidine.

12. The nucleoside phosphate of claim 10 wherein said antineoplastic agent is selected from the group consisting of 2'-deoxy-2',2'-difluorocytidine (gemcitibine), (E)-2'-deoxy-2'-fluoromethylene-cytidine (FMdC), or 1-(2-deoxy-2-fluoro-4-thio-β-D-arabinosyl)cytosine (4'-thio-FAC), Ara-C, Ara-G, 5-fluorouridine, 5-fluoro-deoxyuridine, (R)-deoxycoformycin, and fludarabine.

13. A pharmaceutical composition comprising a nucleoside phosphate according to claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,994,143 B2 | Page 1 of 1 |
| APPLICATION NO. | : 12/797327 | |
| DATED | : August 9, 2011 | |
| INVENTOR(S) | : Karl Y. Hostetler | |

It is certified that error appears in the above-identified patent and that said Letters Patent is hereby corrected as shown below:

On the Title page, item [75]:

Inventor Karl Y. Hostetler residence should be listed as Del Mar, CA (US).

Signed and Sealed this
Eighteenth Day of October, 2011

David J. Kappos
*Director of the United States Patent and Trademark Office*